(12) United States Patent
Ameri et al.

(10) Patent No.: US 7,556,821 B2
(45) Date of Patent: Jul. 7, 2009

(54) APPARATUS AND METHOD FOR TRANSDERMAL DELIVERY OF PARATHYROID HORMONE AGENTS

(75) Inventors: Mahmoud Ameri, Fremont, CA (US); Michel J. N. Cormier, Mountain View, CA (US); Yuh-Fun Maa, Millbrae, CA (US); Marika Kamberi, San Jose, CA (US); Peter Daddona, Menlo Park, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 11/084,634

(22) Filed: Mar. 18, 2005

(65) Prior Publication Data

US 2005/0256045 A1   Nov. 17, 2005

Related U.S. Application Data

(60) Provisional application No. 60/643,660, filed on Jan. 12, 2005, provisional application No. 60/585,276, filed on Jul. 1, 2004, provisional application No. 60/571,304, filed on May 13, 2004.

(51) Int. Cl.
    *A61K 9/00* (2006.01)
    *A61M 5/00* (2006.01)
    *A61K 38/29* (2006.01)
    *C07K 2/00* (2006.01)

(52) U.S. Cl. .................. 424/423; 514/2; 530/300

(58) Field of Classification Search ............. 604/20–22, 604/46–48, 173; 424/400, 422, 423, 426, 424/428; 435/173.4–176.3
See application file for complete search history.

(56) References Cited

U.S. PATENT DOCUMENTS

| | | | |
|---|---|---|---|
| 2,619,962 A | 12/1952 | Rosenthal | |
| 2,893,392 A | 7/1959 | Wagner et al. | |
| 3,072,122 A | 1/1963 | Rosenthal | |
| 3,123,212 A | 3/1964 | Taylor et al. | |
| RE25,637 E | 9/1964 | Kravitz et al. | |
| 3,221,739 A | 12/1965 | Rosenthal | |
| 3,221,740 A | 12/1965 | Rosenthal | |
| 3,678,150 A | 7/1972 | Szumski et al. | |
| 3,814,097 A | 6/1974 | Ganderton et al. | |
| 3,964,482 A | 6/1976 | Gerstel et al. | |
| 4,086,196 A | 4/1978 | Tregear | |
| 4,698,328 A | 10/1987 | Neer et al. | |
| 4,714,621 A | 12/1987 | Gullberg | |
| 4,833,125 A | 5/1989 | Neer et al. | |
| 5,066,494 A | 11/1991 | Becher | |
| 5,080,646 A | 1/1992 | Theeuwes et al. | |
| 5,147,296 A | 9/1992 | Theeuwes et al. | |
| 5,169,382 A | 12/1992 | Theeuwes et al. | |
| 5,169,383 A | 12/1992 | Gyory et al. | |
| 5,208,041 A | 5/1993 | Sindrey | |
| 5,225,098 A * | 7/1993 | Kacher et al. | 510/146 |
| 5,250,023 A | 10/1993 | Lee et al. | |
| 5,382,658 A | 1/1995 | Kronis et al. | |
| 5,496,801 A | 3/1996 | Holthuis et al. | |
| 5,510,370 A | 4/1996 | Hock | |
| 5,563,122 A | 10/1996 | Endo et al. | |
| 5,599,822 A | 2/1997 | Cullinan et al. | |
| 5,629,019 A * | 5/1997 | Lee et al. | 424/489 |
| 5,670,514 A | 9/1997 | Audia et al. | |
| 5,679,647 A | 10/1997 | Carson et al. | |
| 5,738,728 A | 4/1998 | Tisone | |
| 5,741,554 A | 4/1998 | Tisone | |
| 5,743,960 A | 4/1998 | Tisone | |
| 5,747,456 A | 5/1998 | Chorev et al. | |
| 5,770,220 A | 6/1998 | Meconi et al. | |
| 5,785,978 A * | 7/1998 | Porter et al. | 424/401 |
| 5,840,690 A | 11/1998 | Holick | |
| 5,879,326 A | 3/1999 | Godshall et al. | |
| 5,880,093 A | 3/1999 | Bagnoli | |
| 5,916,524 A | 6/1999 | Tisone | |
| 5,935,607 A | 8/1999 | Silver | |
| 5,983,136 A | 11/1999 | Kamen | |
| 6,050,988 A | 4/2000 | Zuck | |
| 6,083,196 A | 7/2000 | Trautman et al. | |
| 6,091,975 A | 7/2000 | Doddona et al. | |
| 6,147,186 A | 11/2000 | Gardella et al. | |
| 6,230,051 B1 | 5/2001 | Cormier et al. | |
| 6,239,144 B1 | 5/2001 | Galvin et al. | |
| 6,274,166 B1 | 8/2001 | Sintov et al. | |
| 6,322,808 B1 | 11/2001 | Trautman et al. | |
| 6,331,310 B1 | 12/2001 | Roser et al. | |
| 6,342,477 B1 | 1/2002 | Tamura et al. | |
| 6,379,324 B1 | 4/2002 | Gartstein et al. | |
| 6,440,096 B1 | 8/2002 | Lastovich et al. | |
| 6,454,755 B1 | 9/2002 | Godshall | |
| 6,537,242 B1 | 3/2003 | Palmer | |

(Continued)

FOREIGN PATENT DOCUMENTS

EP   1 358 896   11/2003

(Continued)

OTHER PUBLICATIONS

O. Braun-Falco and H.C. Korting. Hautarzt (1986) 37(3), pp. 126-129- English Abstract.*

(Continued)

*Primary Examiner*—Andrew D Kosar
(74) *Attorney, Agent, or Firm*—Edwards Angell Palmer & Dodge LLP; Kathleen Williams

(57) ABSTRACT

An apparatus and method for transdermally delivering a biologically active agent comprising a delivery system having a microprojection member (or system) that includes a plurality of microprojections (or array thereof) that are adapted to pierce through the stratum corneum into the underlying epidermis layer, or epidermis and dermis layers. In one embodiment, the PTH-based agent is contained in a biocompatible coating that is applied to the microprojection member.

2 Claims, 9 Drawing Sheets

U.S. PATENT DOCUMENTS

| | | |
|---|---|---|
| 6,537,965 B1 * | 3/2003 | Bringhurst et al. ............. 514/2 |
| 6,565,532 B1 | 5/2003 | Yuzhakov et al. |
| 6,589,202 B1 | 7/2003 | Powell |
| 6,590,081 B1 | 7/2003 | Zhang |
| 6,652,478 B1 | 11/2003 | Gartstein et al. |
| 6,689,100 B2 | 2/2004 | Connelly et al. |
| 6,743,211 B1 | 6/2004 | Prausnitz et al. |
| 6,770,623 B1 | 8/2004 | Chang et al. |
| 6,811,792 B2 | 11/2004 | Roser et al. |
| 6,835,184 B1 | 12/2004 | Sage et al. |
| 6,855,131 B2 | 2/2005 | Trautman et al. |
| 6,855,372 B2 | 2/2005 | Trautman et al. |
| 6,881,203 B2 | 4/2005 | Delmore |
| 6,884,427 B1 | 4/2005 | Barrows |
| 6,918,901 B1 | 7/2005 | Theeuwes et al. |
| 6,931,277 B1 | 8/2005 | Yuzhakov et al. |
| 6,953,589 B1 | 10/2005 | Trautman et al. |
| 6,956,022 B2 | 10/2005 | Tamura et al. |
| 6,977,077 B1 | 12/2005 | Hock et al. |
| 7,097,631 B2 | 8/2006 | Trautman et al. |
| 7,131,960 B2 | 11/2006 | Trautman et al. |
| 7,184,826 B2 | 2/2007 | Cormier et al. |
| 2002/0025929 A1 | 2/2002 | Sato |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0107200 A1 | 8/2002 | Chang et al. |
| 2002/0128599 A1 | 9/2002 | Cormier et al. |
| 2002/0132054 A1 | 9/2002 | Trautman et al. |
| 2002/0177839 A1 * | 11/2002 | Cormier et al. ............. 604/500 |
| 2003/0100885 A1 | 5/2003 | Pettis et al. |
| 2003/0135201 A1 | 7/2003 | Gonnelli |
| 2003/0144209 A1 | 7/2003 | Bringhurst et al. |
| 2003/0181936 A1 | 9/2003 | Trautman et al. |
| 2003/0199810 A1 | 10/2003 | Trautman et al. |
| 2003/0199811 A1 | 10/2003 | Sage, Jr. et al. |
| 2003/0225000 A1 | 12/2003 | Chang et al. |
| 2004/0005668 A1 | 1/2004 | Gautvik et al. |
| 2004/0033950 A1 | 2/2004 | Hock et al. |
| 2004/0062813 A1 | 4/2004 | Cormier et al. |
| 2004/0138610 A1 | 7/2004 | Cormier et al. |
| 2004/0236271 A1 | 11/2004 | Theeuwes et al. |
| 2004/0242489 A1 | 12/2004 | Mitlak |
| 2004/0265354 A1 | 12/2004 | Ameri et al. |
| 2004/0265365 A1 | 12/2004 | Daddona et al. |
| 2005/0008683 A1 | 1/2005 | Mikszta et al. |
| 2005/0009147 A1 | 1/2005 | Bauer et al. |
| 2005/0070473 A9 | 3/2005 | Manolagas et al. |
| 2005/0084604 A1 | 4/2005 | Trautman et al. |
| 2005/0106209 A1 | 5/2005 | Ameri et al. |
| 2005/0106227 A1 | 5/2005 | Zalipsky et al. |
| 2005/0113303 A1 | 5/2005 | Karaplis et al. |
| 2005/0123507 A1 | 6/2005 | Ameri et al. |
| 2005/0148926 A1 | 7/2005 | Trautman et al. |
| 2005/0192227 A1 | 9/2005 | Hock |
| 2005/0255537 A1 | 11/2005 | Hock et al. |
| 2006/0047243 A1 | 3/2006 | Rosenberg |
| 2006/0074377 A1 | 4/2006 | Cormier et al. |
| 2006/0177494 A1 | 8/2006 | Cormier et al. |

FOREIGN PATENT DOCUMENTS

| | | |
|---|---|---|
| EP | 1 301 238 | 9/2004 |
| EP | 1557176 A1 | 7/2005 |
| EP | 1 517 722 | 8/2006 |
| GB | 878788 | 10/1961 |
| GB | 0017999.4 | 7/2000 |
| WO | WO 93/17754 | 9/1993 |
| WO | WO-96/03978 | 2/1996 |
| WO | WO-96/10630 | 4/1996 |
| WO | WO 96/17648 | 7/1996 |
| WO | WO 96/37155 | 11/1996 |
| WO | WO 96/37256 | 11/1996 |
| WO | WO 97/03718 | 2/1997 |
| WO | WO-97/48440 | 12/1997 |
| WO | WO 97/48440 | 12/1997 |
| WO | WO 97/48441 | 12/1997 |
| WO | WO 97/48442 | 12/1997 |
| WO | WO 98/00193 | 1/1998 |
| WO | WO 98/11937 | 3/1998 |
| WO | WO 98/28037 | 7/1998 |
| WO | WO-98/28037 | 7/1998 |
| WO | WO 98/29298 | 7/1998 |
| WO | WO 98/29365 | 7/1998 |
| WO | WO-99/64580 | 12/1999 |
| WO | WO 99/64580 | 12/1999 |
| WO | WO-00/12173 | 3/2000 |
| WO | WO-00/35530 | 6/2000 |
| WO | WO-00/44438 | 8/2000 |
| WO | WO 0187276 A1 * | 11/2001 |
| WO | WO 02/07813 | 1/2002 |
| WO | WO-02/07813 | 1/2002 |
| WO | WO-02/074173 | 9/2002 |
| WO | WO 03/099849 A2 | 12/2003 |
| WO | WO 2005/007184 A2 | 1/2005 |
| WO | WO 2006/006674 A1 | 1/2006 |
| WO | WO 2006/052991 A2 | 5/2006 |

OTHER PUBLICATIONS

S. Mitragotri. Pharm. Res. (2000) 17(11), pp. 1354-1359.*
L. Brannon-Peppas. Med. Plastics Biomat. (1997), 13 pages HTML document.*
D.R. Friend. Crit. Rev. Ther. Drug Carrier Syst. (1990) 7(2), pp. 149-186.*
Codrons et al.., Impact of Formulation and Method of Pulmonary Delivery on Absorption of Parathyroid Hormone (1-34) from Rat Lungs, Journal of Pharmaceutical Sciences, 93(5):1241-1252, 2004.
Pfutzner et al., Pilot Study with Technosphere/PTH(1-34) A new Approach for Effective Pulmonary Delivery of Parathyroid Homone (1-34), Horm. Metab. Res., 35(5):319-23, 2003.
Suzuki et al., Prevention of Bone Loss in Ovariectomized Rats by Pulsatile Transdermal Iontophoretic Administration of Human PTH(1-34), Journal of Pharmaceutical Sceinces, 91(2):350-361, 2002.
Patton, Pulmonary Delivery of Drugs for Bone Disorders, Advance Drug Delivery Reviews 42(3):239-248, 2002.
Chang et al., The Effect of Electroporation on Iontophoretic Transdermal Delivery of Calcium Regulating Hormones, Journal of Controlled Release, 66(2-3):127-133, 2000.
Patton et al., Bioavailability of Pulmonary Delivered Peptides and Proteins: Interferon, Calcitonins and Parathyroid Hormones, Journal of Controlled Release, 28(1-3):79-85, 1994.
Codrons, et al. Systemic delivery of parathyroid hormone (1-34) using inhalation dry powders in rats. J Pharm Sci. 2003; 92(5):938-50.
Gribbon, et al., "Stabilisation of Vaccines Using Trehalose (Q-T4) Technology", Brown F(ed): New Approaches to Stabilisation of Vaccines Potency, Dev Biol Stand. Basel, Karger, 1996, vol. 87, pp. 193-199.
Franks, "Solid aqueous solutions", Pure & Appl. Chem., vol. 65, No. 12, pp. 2527-2537, 1993.
Colaco et al., Research/"Extraordinary Stability of Enzymes Dried in Trehalose: Simplified Molecular Biology", Bio/Technology vol. 10 Sep. 1992, pp. 1007-1011.
"Report of the Technical Review Group Meeting", WHO, Jun. 7-8, 1999, pp. 1-88.
"A plethora of hi-tech vaccines-genetic, edible, sugar glass, and more", Children's Vaccine Initiative, CVI Forum 18, 1999, pp. 1-24.
"Report on the first meeting of the steering committee on Immunization Safety", WHO Geneva, Oct. 25-26, 1999, pp. 1-44.
Roberts, et al., "Solute Structure as a Determinant of Iontophoretic Transport", Mechanisms of Transdermal Drug Delivery, R.O. Potts and R.H. Guy (Ed.), Marcel Dekker (1997) 291-349.

Chang, et al., "Use of Subambient Thermal Analysis to Optimize Protein Lyophilization", Cryobiology 29, (1992), pp. 632-656.

Wang, "Lyophilization and development of solid protein pharmaceuticals", International Journal of Pharmaceutics 203 (2000), pp. 1-60.

Carpenter, et al., "Rational Design of Stable Lyophilized Protein Formulations: Some Practical Advice", Pharmaceutical Research vol. 14, No. 8, 1997, pp. 969-975.

Huang, et al., "Microencapsulation for Gene Delivery", Encyclopedia of Controlled Drug Delivery, John Wiley & Sons, Inc. (1999), pp. 546-553.

General Policy Issues, "Wider access to HIV drugs now a reality", WHO Drug Information, vol. 12, No. 2, 1998, pp. 67-99.

Roos, "Melting and glass transitions of low molecular weight carbohydrates", Carbohydrate Research, 238, (1993), pp. 39-48.

Schunk et al., "Liquid film coating"; Scientific principles and their technological implications, Kistler and Schweizer; Editors, Chapan & Hall, London (1997), pp. 673-708.

"HIV/PPD Conjugate Vaccine Active in Clinical Trial" (1998).

"Glass pharmacy", New Science Publications, Mar. 8, 1997, pp. 24-27.

Fox, "Putting Proteins Under Glass", Science, vol. 267, Mar. 31, 1999, pp. 1922-1923.

Henry et al., "Microfabricated Microneedles: A Novel Approach to Transdermal Drug Delivery", Journal of Pharmaceutical Sciences, vol. 87, No. 8, Aug. 1998, pp. 922-925.

Rola, Ph.D., "Immunizing Agents and Diagnostic Skin Antigens", Remington's 17th Edition, Pharmaceutical Sciences (1985), pp. 1380-1395, Mack Publishing Company, Pennsylvania.

* cited by examiner

APPARATUS AND METHOD FOR TRANSDERMAL DELIVERY OF PARATHYROID HORMONE AGENTS

CROSS-REFERENCE TO RELATED APPLICATIONS

This application claims the benefit of U.S Provisional Application No. 60/571,304, filed May 13, 2004, U.S Provisional Application No. 60/585,276, filed Jul. 1, 2004 and U.S Provisional Application No. 60/643,660, filed Jan. 12, 2005.

FIELD OF THE PRESENT INVENTION

The present invention relates generally to transdermal agent delivery systems and methods. More particularly, the invention relates to an apparatus and method for transdermal delivery of parathyroid hormone agents.

BACKGROUND OF THE INVENTION

Active agents (or drugs) are most conventionally administered either orally or by injection. Unfortunately, many active agent are completely ineffective or have radically reduced efficacy when orally administered, since they either are not absorbed or are adversely affected before entering the bloodstream and thus do not possess the desired activity. On the other hand, the direct injection of the agent intravenously or subcutaneously, while assuring no modification of the agent during administration, is a difficult, inconvenient, painful and uncomfortable procedure that sometimes results in poor patient compliance.

Hence, in principle, transdermal delivery provides for a method of administering active agents that would otherwise need to be delivered via hypodermic injection or intravenous infusion. The word "transdermal", as used herein, is generic term that refers to delivery of an active agent (e.g., a therapeutic agent, such as a drug or an immunologically active agent, such as a vaccine) through the skin to the local tissue or systemic circulatory system without substantial cutting or penetration of the skin, such as cutting with a surgical knife or piercing the skin with a hypodermic needle. Transdermal agent delivery includes delivery via passive diffusion as well as delivery based upon external energy sources, such as electricity (e.g., iontophoresis) and ultrasound (e.g., phonophoresis).

Passive transdermal agent delivery systems, which are more common, typically include a drug reservoir that contains a high concentration of an active agent. The reservoir is adapted to contact the skin, which enables the agent to diffuse through the skin and into the body tissues or bloodstream of a patient.

As is well known in the art, the transdermal drug flux is dependent upon the condition of the skin, the size and physical/chemical properties of the drug molecule, and the concentration gradient across the skin. Because of the low permeability of the skin to many drugs, transdermal delivery has had limited applications. This low permeability is attributed primarily to the stratum corneum, the outermost skin layer which consists of flat, dead cells filled with keratin fibers (i.e., keratinocytes) surrounded by lipid bilayers. This highly-ordered structure of the lipid bilayers confers a relatively impermeable character to the stratum corneum.

One common method of increasing the passive transdermal diffusional agent flux involves pre-treating the skin with, or co-delivering with the agent, a skin permeation enhancer. A permeation enhancer, when applied to a body surface through which the agent is delivered, enhances the flux of the agent therethrough. However, the efficacy of these methods in enhancing transdermal protein flux has been limited, at least for the larger proteins, due to their size.

There also have been many techniques and devices developed to mechanically penetrate or disrupt the outermost skin layers thereby creating pathways into the skin in order to enhance the amount of agent being transdermally delivered. Illustrative is the drug delivery device disclosed in U.S. Pat. No. 3,964,482.

Other systems and apparatus that employ tiny skin piercing elements to enhance transdermal agent delivery are disclosed in U.S. Pat. Nos. 5,879,326, 3,814,097, 5,250,023, 3,964,482, Reissue 25,637, and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365; all incorporated herein by reference in their entirety.

The disclosed systems and apparatus employ piercing elements of various shapes and sizes to pierce the outermost layer (i.e., the stratum corneum) of the skin. The piercing elements disclosed in these references generally extend perpendicularly from a thin, flat member, such as a pad or sheet. The piercing elements in some of these devices are extremely small, some having a microprojection length of only about 25-400 microns and a microprojection thickness of only about 5-50 microns. These tiny piercing/cutting elements make correspondingly small microslits/microcuts in the stratum corneum for enhancing transdermal agent delivery therethrough.

The disclosed systems further typically include a reservoir for holding the agent and also a delivery system to transfer the agent from the reservoir through the stratum corneum, such as by hollow tines of the device itself. One example of such a device is disclosed in WO 93/17754, which has a liquid agent reservoir. The reservoir must, however, be pressurized to force the liquid agent through the tiny tubular elements and into the skin. Disadvantages of such devices include the added complication and expense for adding a pressurizable liquid reservoir and complications due to the presence of a pressure-driven delivery system.

As disclosed in U.S. patent application Ser. No. 10/045, 842, which is fully incorporated by reference herein, it is possible to have the active agent that is to be delivered coated on the microprojections instead of contained in a physical reservoir. This eliminates the necessity of a separate physical reservoir and developing an agent formulation or composition specifically for the reservoir.

As is well known in the art, osteoporosis is a bone disorder characterized by progressive bone loss that predisposes an individual to an increased risk of fracture, typically in the hip, spine and wrist. The progressive bone loss, which typically begins between the ages of 30 and 40, is mainly asymptomatic until a bone fracture occurs, leading to a high degree of patient morbidity and mortality. Eighty percent of those affected by osteoporosis are women and, based on recent studies, during the six years following the onset of menopause, women lose one third of their bone mass.

As is also well known in the art, parathyroid hormone (PTH) is a hormone secreted by the parathyroid gland that regulates the metabolism of calcium and phosphate in the body. PTH has stirred great interest in the treatment of osteoporosis for its ability to promote bone formation and, hence, dramatically reduced incidence of fractures. Large-scale clinical trials have shown that PTH effectively and safely reduces the percentage of vertebral and non-vertebral fractures in women with osteoporosis.

PTH-based agents have also stirred interest in the treatment of bone fractures (in both men and women) by virtue of their ability to accelerate bone healing.

To this end, various stabilized formulations of PTH-based agents have been developed that can be reconstituted for subcutaneous injection, which, as discussed below, is the conventional means of delivery. Illustrative are the formulations disclosed in U.S. Pat. No. 5,563,122 ("Stabilized Parathyroid Hormone Composition") and U.S. Patent Application Pub. No. 2002/0107200 ("Stabilized Teriparatide Solutions"), which are incorporated by reference herein in their entirety.

A currently approved injectable PTH-based agent is FORTEO™ (an rDNA derived teriparatide injection), which contains recombinant human parathyroid hormone (1-34), (rhPTH (1-34)). FORTEO™ is typically prescribed for women with a history of osteoporotic fracture, who have multiple risk factors for fracture, or who have failed or are intolerant of previous osteoporosis therapy, based on a physician's assessment. In postmenopausal women with osteoporosis, FORTEO™ has been found to increase bone mineral density (BMD) and reduce the risk of vertebral and non-vertebral fractures.

FORTEO™ has also been found to increase bone mass in men with primary or hypogonadal osteoporosis who are at high risk for fracture. These include men with a history of osteoporotic fracture, or who have multiple risk factors for fracture, or who have failed or are intolerant to previous osteoporosis therapy. In men with primary or hypogonadal osteoporosis, FORTEO™ has similarly been found to increase BMD.

In addition to subcutaneous injection, other means of delivering PTH-based agents have also been investigated. For example, various pulmonary delivery (i.e., inhalation) methods are discussed in "Pulmonary Delivery of Drugs for Bone Disorders," *Advanced Drug Delivery Reviews*, Vol. 42, Issue 3, pp. 239-248 (Aug. 31, 2000), Patton, "Bioavailability of Pulmonary Delivered Peptides and Proteins:—Interferon, Calcitonins and Parathyroid Hormones," *Journal of Controlled Release*, Vol. 28, Issues 1-3, pp. 79-85 (January 1994), Patton, et al., "Impact of Formulation and Methods of Pulmonary Delivery on Absorption of Parathyroid Hormone (1-34) from Rat Lungs," *Journal of Pharmaceutical Sciences*, Vol. 93, Issue 5, pp. 1241-1252 (May 2004), Codrons, et al., "Systemic Delivery of Parathyroid Hormone (1-34) Using Inhalation Dry Powders in Rats," *Journal of Pharmaceutical Sciences*, Vol. 92, Issue 5, pp. 938-950 (May 2003) and Pfützner, A, et al., "Pilot Study with Technosphere/PTH(1-34)—A New Approach for Effective Pulmonary Delivery of Parathyroid Hormone (1-34)", *Horm. Metab. Res.*, Vol. 35(5), pp. 319-23.

Various methods of active transdermal delivery of PTH-based agents are also discussed in "The Effect of Electroporation on Eontophoretic Eransdermal Delivery of Calcium Regulating Hormones," *Journal of Controlled Release*, Vol. 66, Issues 2-3, pp. 127-133 (May 15, 2000) and Chang, et al., "Prevention of Bone Loss in Ovariectomized Rats by Pulsatile Transdermal Iontophoretic Administration of Human PTH(1-34)," *Journal of Pharmaceutical Sciences*, Vol. 91, Issue 2, pp.350-361 (February 2002).

Despite the efficacy of PTH in treating disorders such as osteoporosis, there are several drawbacks and disadvantages associated with the disclosed prior art methods of delivering PTH, particularly, via subcutaneous injection. A major drawback is that subcutaneous injection is a difficult and uncomfortable procedure, which often results in poor patient compliance.

Intracutaneous administration of agents, such as hGH, using microprojection systems has previously been documented to provide a pharmacokinetic profile of hGH similar to that observed following subcutaneous administration. See, e.g., Cormier, et al., U.S. Patent Application Pub. No. 2002/0128599, entitled "Transdermal Drug Delivery Devices Having Coated Microprotrusions".

Continuous infusion of a PTH-based agent in vivo results in active bone resorption. It is therefore of critical importance that the PTH-based agent be administered in a pulsatile fashion. Based on the efficacy results from the once daily subcutaneous injection, any alternative route of PTH delivery should provide blood concentration of PTH no slower than that for subcutaneously injected PTH.

It would thus be desirable to provide an agent delivery system that facilitates minimally invasive administration of PTH-based agents. It would further be desirable to provide an agent delivery system that provides a pharmacokinetic profile of the PTH-based agent similar to that observed following subcutaneous administration.

It is therefore an object of the present invention to provide a transdermal agent delivery apparatus and method that provides intracutaneous delivery of a PTH-based agent to a patient.

It is another object of the invention to provide a transdermal agent delivery apparatus and method that provides a pharmacokinetic profile of the PTH-based agent similar to or faster than that observed following subcutaneous administration.

It is another object of the invention to provide a transdermal agent delivery apparatus and method that provides pharmacologically active blood concentration of a PTH-based agent for a period of up to eight hours.

It is another object of the invention to provide a PTH-based agent formulation for intracutaneous delivery to a patient.

It is another object of the present invention to provide a transdermal agent delivery apparatus and method that includes microprojections coated with a biocompatible coating that includes at least one biologically active agent, preferably, a PTH-based agent.

SUMMARY OF THE INVENTION

In accordance with the above objects and those that will be mentioned and will become apparent below, the apparatus and method for transdermally delivering a PTH-based agent in accordance with this invention generally comprises a delivery system having a microprojection member (or system) that includes a plurality of microprojections (or array thereof) that are adapted to pierce through the stratum corneum into the underlying epidermis layer, or epidermis and dermis layers. In a preferred embodiment, the microprojection member includes a biocompatible coating having at least one PTH-based agent disposed therein.

In one embodiment of the invention, the microprojection member has a microprojection density of at least approximately 10 microprojections/cm$^2$, more preferably, in the range of at least approximately 200-2000 microprojections/cm$^2$.

In one embodiment, the microprojection member is constructed out of stainless steel, titanium, nickel titanium alloys, or similar biocompatible materials.

In another embodiment, the microprojection member is constructed out of a non-conductive material, such as a polymeric material. Alternatively, the microprojection member can be coated with a non-conductive material, such as Parylene®, or a hydrophobic material, such as Teflon®, silicon or other low energy material.

The coating formulations applied to the microprojection member to form solid biocompatible coatings can comprise aqueous and non-aqueous formulations. Preferably, the coating formulations include at least one PTH-based agent, which can be dissolved within a biocompatible carrier or suspended within the carrier.

In a preferred embodiment, the PTH-based agent is selected from the group consisting of hPTH(1-34), hPTH salts and analogs, teriparatide and related peptides. Throughout this application, the terms "PTH-based agent" and "hPTH (1-34) agent" include, without limitation, recombinant hPTH (1-34), synthetic hpTH(1-34), PTH(1-34), teriparatide, hPTH(1-34) salts, simple derivatives of hPTH(1-34), such as hPTH(1-34) amide, and closely related molecules, such as hPTH(1-33) or hPTH(1-31) amide, or any other closely related osteogenic peptide. Synthetic hPTH(1-34) is the most preferred PTH agent.

Examples of pharmaceutically acceptable hPTH salts include, without limitation, acetate, propionate, butyrate, pentanoate, hexanoate, heptanoate, levulinate, chloride, bromide, citrate, succinate, maleate, glycolate, gluconate, glucuronate, 3-hydroxyisobutyrate, tricarballylicate, malonate, adipate, citraconate, glutarate, itaconate, mesaconate, citramalate, dimethylolpropinate, tiglicate, glycerate, methacrylate, isocrotonate, β-hydroxibutyrate, crotonate, angelate, hydracrylate, ascorbate, aspartate, glutamate, 2-hydroxyisobutyrate, lactate, malate, pyruvate, fumarate, tartarate, nitrate, phosphate, benzene, sulfonate, methane sulfonate, sulfate and sulfonate.

Preferably, the PTH-based agent is present in the coating formulation at a concentration in the range of approximately 1-30 wt. %.

More preferably, the amount of PTH-based agent contained in the solid biocompatible coating (i.e., microprojection member or product) is in the range of approximately 1 μg-1000 μg, even more preferably, in the range of approximately 10-100 μg.

Also preferably, the pH of the coating formulation is below approximately pH 6. More preferably, the coating formulation has a pH in the range of approximately pH 2-pH 6. Even more preferably, the coating formulation has a pH in the range of approximately pH 3-pH 6.

In certain embodiments of the invention, the viscosity of the coating formulation that is employed to coat the microprojections is enhanced by adding low volatility counterions. In one embodiment, the PTH-based agent has a positive charge at the formulation pH and the viscosity-enhancing counterion comprises an acid having at least two acidic pKas. Suitable acids include maleic acid, malic acid, malonic acid, tartaric acid, adipic acid, citraconic acid, fumaric acid, glutaric acid, itaconic acid, meglutol, mesaconic acid, succinic acid, citramalic acid, tartronic acid, citric acid, tricarballylic acid, ethylenediaminetetraacetic acid, aspartic acid, glutamic acid, carbonic acid, sulfuric acid and phosphoric acid.

Another preferred embodiment is directed to a viscosity-enhancing mixture of counterions, wherein the PTH-based agent has a positive charge at the formulation pH and at least one of the counterion comprises an acid having at least two acidic pKas. The other counterion comprises an acid with one or more pKas. Examples of suitable acids include hydrochloric acid, hydrobromic acid, nitric acid, sulfuric acid, maleic acid, phosphoric acid, benzene sulfonic acid, methane sulfonic acid, citric acid, succinic acid, glycolic acid, gluconic acid, glucuronic acid, lactic acid, malic acid, pyruvic acid, tartaric acid, tartronic acid, fumaric acid, acetic acid, propionic acid, pentanoic acid, carbonic acid, malonic acid, adipic acid, citraconic acid, levulinic acid, glutaric acid, itaconic acid, meglutol, mesaconic acid, citramalic acid, citric acid, aspartic acid, glutamic acid, tricarballylic acid and ethylenediaminetetraacetic acid.

In the noted embodiments of the invention, the amount of counterion is preferably sufficient to neutralize the charge of the PTH. In such embodiments, the amount of the counterion or mixture of counterions is preferably sufficient to neutralize the charge present on the agent at the pH of the formulation. In additional embodiments, excess counterion (as the free acid or as a salt) is added to the peptide to control pH and provide adequate buffering capacity.

In another preferred embodiment, the agent comprises hPTH (1-34) and the counterion comprises a viscosity-enhancing mixture of counterions chosen from the group consisting of citric acid, tartaric acid, malic acid, hydrochloric acid, glycolic acid and acetic acid. Preferably, the counterions are added to the formulation to achieve a viscosity in the range of approximately 20-200 cp.

In a preferred embodiment of the invention, the viscosity-enhancing counterion comprises an acidic counterion, such as a low volatility weak acid that exhibits at least one acidic pKa and a melting point higher than about 50° C. or a boiling point higher than about 170° C. at $P_{atm}$. Examples of such acids include citric acid, succinic acid, glycolic acid, gluconic acid, glucuronic acid, lactic acid, malic acid, pyruvic acid, tartaric acid, tartronic acid, and fumaric acid.

In another preferred embodiment, the counterion comprises a strong acid that exhibits at least one pKa lower than about 2. Examples of such acids include hydrochloric acid, hydrobromic acid, nitric acid, sulfonic acid, sulfuric acid, maleic acid, phosphoric acid, benzene sulfonic acid and methane sulfonic acid.

Another preferred embodiment is directed to a mixture of counterions, wherein at least one of the counterion comprises a strong acid and at least one of the counterion comprises a low volatility weak acid.

Another preferred embodiment is directed to a mixture of counterions, wherein at least one of the counterion comprises a strong acid and at least one of the counterion comprises a weak acid having a high volatility and exhibiting at least one pKa higher than about 2 and a melting point lower than about 50° C. or a boiling point lower than about 170° C. at $P_{atm}$. Examples of such acids include acetic acid, propionic acid, pentanoic acid and the like.

The acidic counterion is preferably present in an amount that is sufficient to neutralize the positive charge present on the PTH-based agent at the pH of the formulation. In an additional embodiment, an excess counterion (as the free acid or as a salt) is added to control pH and to provide adequate buffering capacity.

In another embodiment of the invention, the coating formulation includes at least one buffer. Examples of such buffers include, without limitation, ascorbic acid, citric acid, succinic acid, glycolic acid, gluconic acid, glucuronic acid, lactic acid, malic acid, pyruvic acid, tartaric acid, tartronic acid, fumaric acid, maleic acid, phosphoric acid, tricarballylic acid, malonic acid, adipic acid, citraconic acid, glutaratic acid, itaconic acid, mesaconic acid, citramalic acid, dimethylolpropionic acid, tiglic acid, glyceric acid, methacrylic acid, isocrotonic acid, β-hydroxybutyric acid, crotonic acid, angelic acid, hydracrylic acid, aspartic acid, glutamic acid, glycine and mixtures thereof.

In one embodiment of the invention, the coating formulation includes at least one antioxidant, which can comprise sequestering agents, such sodium citrate, citric acid, EDTA (ethylene-dinitrilo-tetraacetic acid) or free radical scavengers, such as ascorbic acid, methionine, sodium ascorbate and the like. Presently preferred antioxidants comprise EDTA and methionine.

In the noted embodiments of the invention, the concentration of the antioxidant is preferably in the range of approximately 0.01-20 wt. % of the coating formulation. More preferably, the concentration of the antioxidant is in the range of approximately 0.03-10 wt. % of the coating formulation.

In one embodiment of the invention, the coating formulation includes at least one surfactant, which can be zwitterionic, amphoteric, cationic, anionic, or nonionic, including, without limitation, sodium lauroamphoacetate, sodium dodecyl sulfate (SDS), cetylpyridinium chloride (CPC), dodecyltrimethyl ammonium chloride (TMAC), benzalkonium, chloride, polysorbates such as Tween 20 and Tween 80, other sorbitan derivatives, such as sorbitan lauratealkoxylated alcohols, such as laureth-4 and polyoxyethylene castor oil derivatives, such as Cremophor EL®.

In the noted embodiments of the invention, the concentration of the surfactant is preferably in the range of approximately 0.01-20 wt. % of the coating formulation. Preferably, the concentration of the surfactant is in the range of approximately 0.05-1 wt. % of the coating formulation.

In a further embodiment of the invention, the coating formulation includes at least one polymeric material or polymer that has amphiphilic properties, which can comprise, without limitation, cellulose derivatives, such as hydroxyethylcellulose (HEC), hydroxypropylmethylcellulose (HPMC), hydroxypropycellulose (HPC), methylcellulose (MC), hydroxyethylmethylcellulose (HEMC), or ethylhydroxy-ethylcellulose (EHEC), as well as pluronics.

In one embodiment of the invention, the concentration of the polymer presenting amphiphilic properties in the coating formulation is preferably in the range of approximately 0.01-20 wt. %, more preferably, in the range of approximately 0.03-10 wt. % of the coating formulation.

In another embodiment, the coating formulation includes a hydrophilic polymer selected from the following group: hydroxyethyl starch, carboxymethyl cellulose and salts of, dextran, poly(vinyl alcohol), poly(ethylene oxide), poly(2-hydroxyethyl-methacrylate), poly(n-vinyl pyrolidone), polyethylene glycol and mixtures thereof, and like polymers.

In a preferred embodiment, the concentration of the hydrophilic polymer in the coating formulation is in the range of approximately 1-30 wt. %, more preferably, in the range of approximately 1-20 wt. % of the coating formulation.

In another embodiment of the invention, the coating formulation includes a biocompatible carrier, which can comprise, without limitation, human albumin, bioengineered human albumin, polyglutamic acid, polyaspartic acid, polyhistidine, pentosan polysulfate, polyamino acids, sucrose, trehalose, melezitose, raffinose and stachyose.

Preferably, the concentration of the biocompatible carrier in the coating formulation is in the range of approximately 2-70 wt. %, more preferably, in the range of approximately 5-50 wt. % of the coating formulation.

In another embodiment, the coating formulation includes a stabilizing agent, which can comprise, without limitation, a non-reducing sugar, a polysaccharide or a reducing sugar.

Suitable non-reducing sugars for use in the methods and compositions of the invention include, for example, sucrose, trehalose, stachyose, or raffinose.

Suitable polysaccharides for use in the methods and compositions of the invention include, for example, dextran, soluble starch, dextrin, and insulin.

Suitable reducing sugars for use in the methods and compositions of the invention include, for example, monosaccharides such as, for example, apiose, arabinose, lyxose, ribose, xylose, digitoxose, fucose, quercitol, quinovose, rhamnose, allose, altrose, fructose, galactose, glucose, gulose, hamamelose, idose, mannose, tagatose, and the like; and disaccharides such as, for example, primeverose, vicianose, rutinose, scillabiose, cellobiose, gentiobiose, lactose, lactulose, maltose, melibiose, sophorose, and turanose and the like.

Preferably, the concentration of the stabilizing agent in the coating formulation is at a ratio of approximately 0.1-2.0:1 with respect to the PTH-based agent, more preferably, approximately 0.25-1.0:1 with respect to the PTH-based agent.

In another embodiment, the coating formulation includes a vasoconstrictor, which can comprise, without limitation, amidephrine, cafaminol, cyclopentamine, deoxyepinephrine, epinephrine, felypressin, indanazoline, metizoline, midodrine, naphazoline, nordefrin, octodrine, omipressin, oxymethazoline, phenylephrine, phenylethanolamine, phenylpropanolamine, propylhexedrine, pseudoephedrine, tetrahydrozoline, tramazoline, tuaminoheptane, tymazoline, vasopressin, xylometazoline and the mixtures thereof. The most preferred vasoconstrictors include epinephrine, naphazoline, tetrahydrozoline indanazoline, metizoline, tramazoline, tymazoline, oxymetazoline and xylometazoline.

The concentration of the vasoconstrictor, if employed, is preferably in the range of approximately 0.1 wt. % to 10 wt. % of the coating formulation.

In another embodiment of the invention, the coating formulation includes at least one "pathway patency modulator", which can comprise, without limitation, osmotic agents (e.g., sodium chloride), zwitterionic compounds (e.g., amino acids), and anti-inflammatory agents, such as betamethasone 21-phosphate disodium salt, triamcinolone acetonide 21-disodium phosphate, hydrocortamate hydrochloride, hydrocortisone 21-phosphate disodium salt, methylprednisolone 21-phosphate disodium salt, methylprednisolone 21-succinaate sodium salt, paramethasone disodium phosphate and prednisolone 21-succinate sodium salt, and anticoagulants, such as citric acid, citrate salts (e.g., sodium citrate), dextrin sulfate sodium, aspirin and EDTA.

In yet another embodiment of the invention, the coating formulation includes a solubilising/complexing agent, which can comprise Alpha-Cyclodextrin, Beta-Cyclodextrin, Gamma-Cyclodextrin, glucosyl-alpha-Cyclodextrin, maltosyl-alpha-Cyclodextrin, glucosyl-beta-Cyclodextrin, maltosyl-beta-Cyclodextrin, hydroxypropyl beta-Cyclodextrin, 2-hydroxypropyl-beta-Cyclodextrin, 2-hydroxypropyl-gamma-Cyclodextrin, hydroxyethyl-beta-Cyclodextrin, methyl-beta-Cyclodextrin, sulfobutylether-alpha-Cyclodextrin, sulfobutylether-beta-Cyclodextrin, and sulfobutylether-gamma-Cyclodextrin. Most preferred solubilising/complexing agents are beta-Cyclodextrin, hydroxypropyl beta-Cyclodextrin, 2-hydroxypropyl-beta-Cyclodextrin and sulfobutylether7 beta-Cyclodextrin.

The concentration of the solubilising/complexing agent, if employed, is preferably in the range of approximately 1 wt. % to 20 wt. % of the coating formulation.

In another embodiment of the invention, the coating formulation includes at least one non-aqueous solvent, such as ethanol, isopropanol, methanol, propanol, butanol, propylene glycol, dimethysulfoxide, glycerin, N,N-dimethylformamide and polyethylene glycol 400. Preferably, the non-aqueous solvent is present in the coating formulation in the range of approximately 1 wt. % to 50 wt. % of the coating formulation.

Preferably, the coating formulations have a viscosity less than approximately 500 centipoise and greater than 3 centipoise.

In one embodiment of the invention, the thickness of the biocompatible coating is less than 25 microns, more preferably, less than 10 microns, as measured from the microprojection surface.

In accordance with one embodiment of the invention, the method for delivering a PTH-based agent to a subject comprises (i) providing a microprojection member having a plurality of stratum corneum-piercing microprojections, the microprojection member having a biocompatible coating disposed thereon that includes at least one PTH-based agent, (ii) applying the microprojection member to a skin site on the subject, whereby the microprojections pierce the stratum corneum and deliver the PTH-based agent to the subject.

Preferably, the coated microprojection member is applied to the skin site via an impact applicator.

Also preferably, the coated microprojection member is preferably left on the skin site for a period lasting from 5 seconds to 24 hours. Following the desired wearing time, the microprojection member is removed. In some embodiments, wherein the PTH-based agent is in the range of approximately 1 μg-1000 μg of the biocompatible coating.

Further, the pharmacokinetic profile of the transdermally delivered PTH-based agent is preferably at least similar to the pharmacokinetic profile observed following subcutaneous delivery.

In one preferred embodiment, the PTH-based agent is selected from the group consisting of hPTH (1-34), hPTH salts and analogs, teriparatide and related peptides. Also preferably, the hPTH salt is selected from group consisting of acetate, propionate, butyrate, pentanoate, hexanoate, heptanoate, levulinate, chloride, bromide, citrate, succinate, maleate, glycolate, gluconate, glucuronate, 3-hydroxyisobutyrate, tricarballylicate, malonate, adipate, citraconate, glutarate, itaconate, mesaconate, citramalate, dimethylolpropinate, tiglicate, glycerate, methacrylate, isocrotonate, β-hydroxibutyrate, crotonate, angelate, hydracrylate, ascorbate, aspartate, glutamate, 2-hydroxyisobutyrate, lactate, malate, pyruvate, fumarate, tartarate, nitrate, phosphate, benzene, sulfonate, methane sulfonate, sulfate and sulfonate In the methods of the invention, transdermal delivery of a PTH-based agent preferably exhibits rapid on-set of biological action. Also preferably, transdermal delivery of a PTH-based agent exhibits sustained biological action for a period of up to 8 hours.

In one embodiment, the transdermally delivered PTH-based agent comprises teriparatide (hPTH (1-34)) and the biocompatible coating comprises a dose of the PTH-based agent in the range of approximately 10-100 μg dose, wherein delivery of the PTH-based agent results in a plasma $C_{max}$ of at least 50 pg/mL after one application.

The invention also comprises a method of improving the pharmacokinetics of a transdermally delivered PTH-based agent comprising providing a microprojection member having a plurality of stratum corneum-piercing microprojections, the microprojection member having a biocompatible coating disposed thereon that includes at least one PTH-based agent and applying the microprojection member to a skin site on the subject, whereby the microprojections pierce the stratum corneum and deliver the PTH-based agent to the subject so that delivery of the PTH-based agent has improved pharmacokinetics compared to the pharmacokinetics characteristic of subcutaneous delivery.

In the noted embodiments, the improved pharmacokinetics can comprise increased bioavailability of the PTH-based agent. The improved pharmacokinetics can also comprise increased in $C_{max}$. Further, the improved pharmacokinetics can comprise decreased $T_{max}$. The improved pharmacokinetics can further comprise an enhanced absorption rate of the PTH-based agent.

The apparatus and method of the invention can thus be employed safely and effectively in the treatment of osteoporosis and bone fractures.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Before describing the present invention in detail, it is to be understood that this invention is not limited to particularly exemplified materials, methods or structures as such may, of course, vary. Thus, although a number of materials and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a," "an" and "the" include plural referents unless the content clearly dictates otherwise. Thus, for example, reference to "an active agent" includes two or more such agents; reference to "a microprojection" includes two or more such microprojections and the like.

Definitions

The term "transdermal", as used herein, means the delivery of an agent into and/or through the skin for local or systemic therapy.

The term "transdermal flux", as used herein, means the rate of transdermal delivery.

Figure 1:
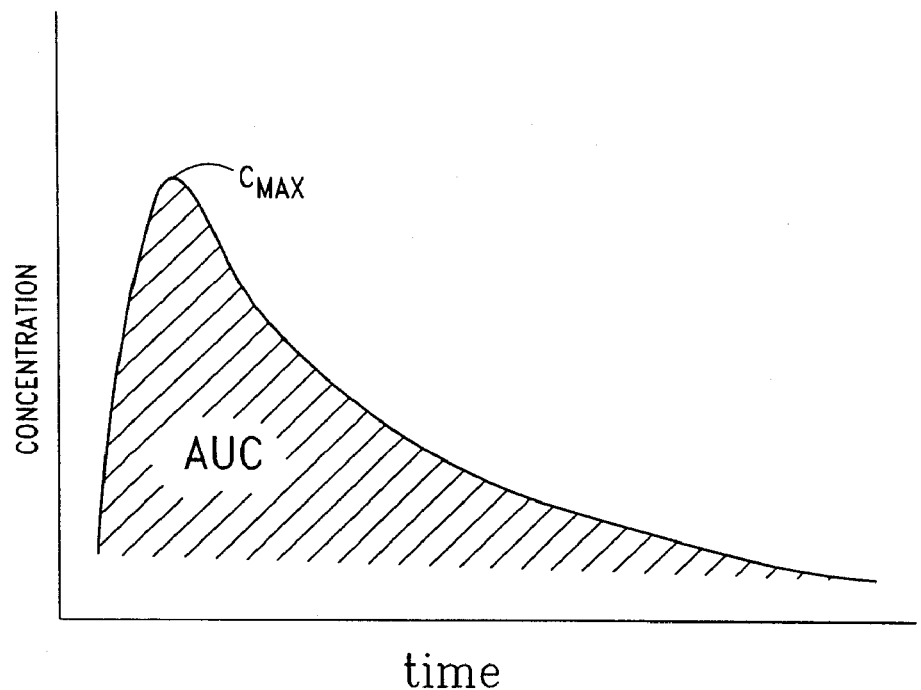
FIG. 1 is a schematic illustration of a pulsatile concentration profile, according to the invention.

The terms "pulsatile delivery profile" and "pulsatile concentration profile", as used herein, mean a post administration increase in blood serum concentration of a PTH-based agent from a baseline concentration to a concentration in the range of approximately 50-1000 pg/mL in a period ranging from 1 min. to 4 hr., wherein $C_{max}$ is achieved, and a decrease in blood serum concentration from $C_{max}$ to the baseline concentration in a period ranging from 1-8 hrs. after $C_{max}$ has been achieved. As illustrated in FIG. 1, the noted concentration (or pharmacokinetic) profile typically reflects a rapid rise in blood serum concentration after administration (i.e., first region) and a slightly less rapid decline (i.e., second region) relative to the first region after $C_{max}$ has been reached, which is generally reflected by a spike in the concentration profile.

Other concentration profiles resulting in a pulsatile delivery comprising a rise in blood concentration of the PTH-based agent to a $C_{max}$ of 50-1000 pg/mL within a twelve-hour period following administration would also likely result in the desired beneficial effect and, hence, are within the scope of the present invention.

As discussed in detail herein, in one embodiment of the invention, the noted "pulsatile delivery profile" is reflected (or evidenced) by a curve of PTH-based agent concentration in the host's blood serum versus time having an area under the curve (AUC) in the range of approximately 0.014-5.24 h·ng/mL and a $C_{max}$ in the range of approximately 0.13-0.72 ng/mL for a microprojection member nominally containing 30 μg PTH(1-34).

The term "co-delivering", as used herein, means that a supplemental agent(s) is administered transdermally either before the PTH-based agent is delivered, before and during transdermal flux of the PTH-based agent, during transdermal flux of the PTH-based agent, during and after transdermal flux of the PTH-based agent, and/or after transdermal flux of the PTH-based agent. Additionally, two or more PTH-based agents may be formulated in the coatings and/or formulations, resulting in co-delivery of the PTH-based agents.

The terms "PTH-based agent" and "hPTH(1-34) agent", as used herein, include, without limitation, hPTH(1-34), hPTH salts, hPTH analogs, teriparatide, closely related peptides and agents having a peptide sequence that functions by the same means as the 34 N-terminal amino acids (the biologically active region) sequence of the 84-amino acid human parathyroid hormone. The terms "PTH-based agent" and "hPTH(1-34) agent" thus include, without limitation, recombinant hPTH(1-34), synthetic hPTH(1-34), PTH(1-34), hPTH(1-34) salts, teriparatide, simple derivatives of hPTH(1-34), such as hPTH(1-34) amide and closely related molecules, such as hPTH(1-33) or hPTH(1-31) amide and closely related osteogenic peptides.

Examples of suitable hPTH salts include, without limitation, acetate, propionate, butyrate, pentanoate, hexanoate, heptanoate, levulinate, chloride, bromide, citrate, succinate, maleate, glycolate, gluconate, glucuronate, 3-hydroxyisobutyrate, tricarballylicate, malonate, adipate, citraconate, glutarate, itaconate, mesaconate, citramalate, dimethylolpropinate, tiglicate, glycerate, methacrylate, isocrotonate, β-hydroxibutyrate, crotonate, angelate, hydracrylate, ascorbate, aspartate, glutamate, 2-hydroxyisobutyrate, lactate, malate, pyruvate, fumarate, tartarate, nitrate, phosphate, benzene, sulfonate, methane sulfonate, sulfate and sulfonate.

The noted PTH-based agents can also be in various forms, such as free bases, acids, charged or uncharged molecules, components of molecular complexes or nonirritating, pharmacologically acceptable salts.

It is to be understood that more than one PTH-based agent can be incorporated into the agent source, reservoirs, and/or coatings of this invention, and that the use of the term "PTH-based agent" in no way excludes the use of two or more such agents.

The term "microprojections", as used herein, refers to piercing elements which are adapted to pierce or cut through the stratum corneum into the underlying epidermis layer, or epidermis and dermis layers, of the skin of a living animal, particularly a mammal and more particularly a human.

In one embodiment of the invention, the piercing elements have a projection length less than 1000 microns. In a further embodiment, the piercing elements have a projection length of less than 500 microns, more preferably, less than 250 microns. The microprojections further have a width (designated "W" in FIG. 1) in the range of approximately 25-500 microns and a thickness in the range of approximately 10-100 microns. The microprojections may be formed in different shapes, such as needles, blades, pins, punches, and combinations thereof.

The term "microprojection member", as used herein, generally connotes a microprojection array comprising a plurality of microprojections arranged in an array for piercing the stratum corneum. The microprojection member can be formed by etching or punching a plurality of microprojections from a thin sheet and folding or bending the microprojections out of the plane of the sheet to form a configuration, such as that shown in FIG. 2. The microprojection member can also be formed in other known manners, such as by forming one or more strips having microprojections along an edge of each of the strip(s) as disclosed in U.S. Pat. No. 6,050,988, which is hereby incorporated by reference in its entirety.

The term "coating formulation", as used herein, is meant to mean and include a freely flowing composition or mixture that is employed to coat the microprojections and/or arrays thereof. Preferably, the coating formulation includes at least one PTH-based agent, which can be in solution or suspension in the formulation.

The term "biocompatible coating" and "solid coating", as used herein, is meant to mean and include a "coating formulation" in a substantially solid state.

As indicated above, the present invention generally comprises a delivery system including microprojection member (or system) having a plurality of microprojections (or array thereof) that are adapted to pierce through the stratum corneum into the underlying epidermis layer, or epidermis and dermis layers.

As discussed in detail herein, a key advantage of the present invention is that the delivery system delivers the PTH-based agent to a mammalian host, particularly, a human patient, whereby the PTH-based agent in the patient's serum after administration exhibits a preferred pulsatile concentration profile. The delivery system is further amenable to self-administration of a 20 μg bolus dose of a PTH-based agent at least once daily.

Figure 2:
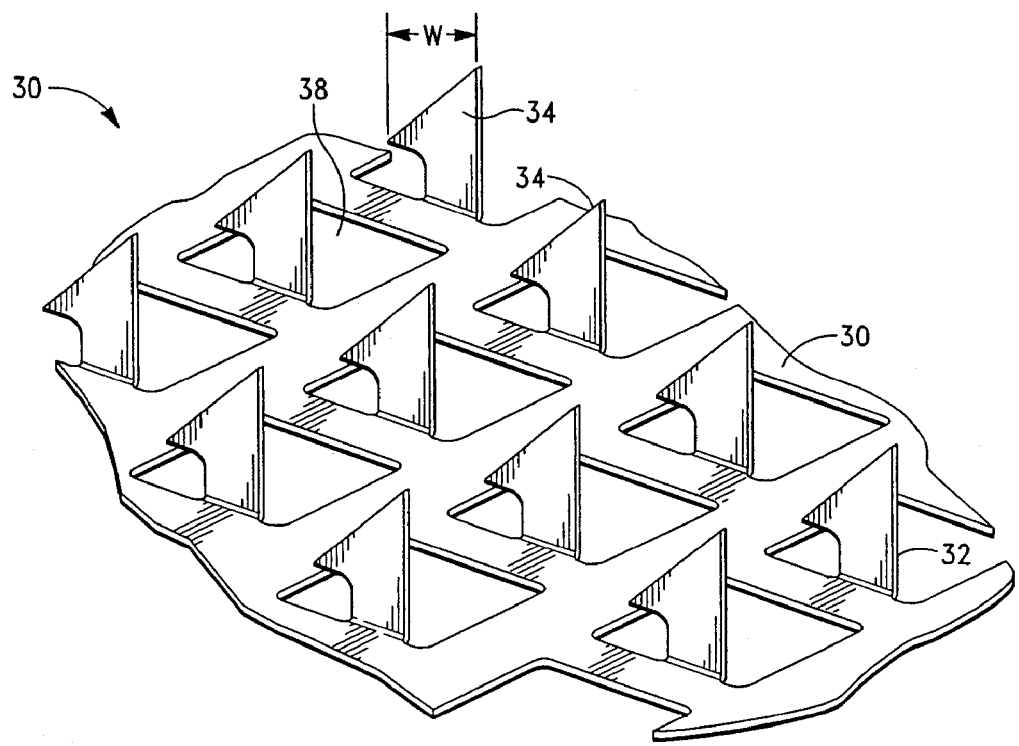
FIG. 2 is a perspective view of a portion of one example of a microprojection member, according to the invention.

Referring now to FIG. 2, there is shown one embodiment of a microprojection member 30 for use with the present invention. As illustrated in FIG. 2, the microprojection member 30 includes a microprojection array 32 having a plurality of microprojections 34. The microprojections 34 preferably extend at substantially a 90° angle from the sheet, which in the noted embodiment includes openings 38.

Figure 4:
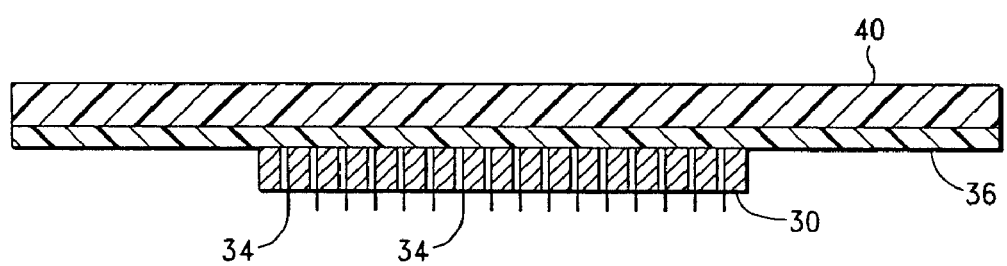
FIG. 4 is a side sectional view of a microprojection member having an adhesive backing, according to the invention.

According to the invention, the sheet 36 can be incorporated into a delivery patch, including a backing 40 for the sheet 36, and can additionally include adhesive 16 for adhering the patch to the skin (see FIG. 4). In this embodiment, the microprojections 34 are formed by etching or punching a plurality of microprojections 34 from a thin metal sheet 36 and bending the microprojections 34 out of the plane of the sheet 36.

In one embodiment of the invention, the microprojection member 30 has a microprojection density of at least approximately 10 microprojections/cm$^2$, more preferably, in the range of at least approximately 200-2000 microprojections/cm$^2$. Preferably, the number of openings per unit area through which the agent passes is at least approximately 10 openings/cm$^2$ and less than about 2000 openings/cm$^2$.

As indicated, the microprojections 34 preferably have a projection length less than 1000 microns. In one embodiment, the microprojections 34 have a projection length of less than 500 microns, more preferably, less than 250 microns. The microprojections 34 also preferably have a width in the range of approximately 25-500 microns and thickness in the range of approximately 10-100 microns.

In further embodiments of the invention, the biocompatibility of the microprojection member 30 can be improved to minimize or eliminate bleeding and irritation following application to the skin of a subject. Specifically, the microprojections 34 can have a length less than 145 microns, more preferably, in the range of approximately 50-145 microns, and even more preferably, in the range of approximately 70-140 microns. Also, the microprojection member 30 comprises an array preferably having a microprojection density greater than 100 microprojections/cm$^2$, and more preferably, in the range of approximately 200-3000 microprojections/cm$^2$. Further details regarding microprojection members having improved biocompatibility are found in U.S. Application Ser. No. 60/653,675, filed Feb. 15, 2005, which is hereby incorporated by reference in its entirety.

The microprojection member 30 can be manufactured from various metals, such as stainless steel, titanium, nickel titanium alloys, or similar biocompatible materials.

According to the invention, the microprojection member 30 can also be constructed out of a non-conductive material, such as a polymeric material. Alternatively, the microprojection member can be coated with a non-conductive material, such as Parylene®, or a hydrophobic material, such as Teflon®, silicon or other low energy material. The noted hydrophobic materials and associated base (e.g., photoreist) layers are set forth in U.S. Application No. 60/484,142, which is incorporated by reference herein in its entirety.

Microprojection members that can be employed with the present invention include, but are not limited to, the members disclosed in U.S. Pat. Nos. 6,083,196, 6,050,988 and 6,091,975, which are incorporated by reference herein in their entirety.

Other microprojection members that can be employed with the present invention include members formed by etching silicon using silicon chip etching techniques or by molding plastic using etched micro-molds, such as the members disclosed U.S. Pat. No. 5,879,326, which is incorporated by reference herein in its entirety.

In certain embodiments of the invention, the microprojections 34 are preferably configured to reduce variability in the applied coating 35. Suitable microprojections generally comprise a location having a maximum width transverse to the longitudinal axis that is located at a position in the range of approximately 25% to 75% of the length of the microprojection from the distal tip. Proximal to the location of maximum width, the width of the microprojection tapers to a minimum width. Further details regarding the noted microprojection configurations are found in U.S. Application Ser. No. 60/649,888, filed Jan. 31, 2005, which is incorporated by reference herein in its entirety.

Figure 3:
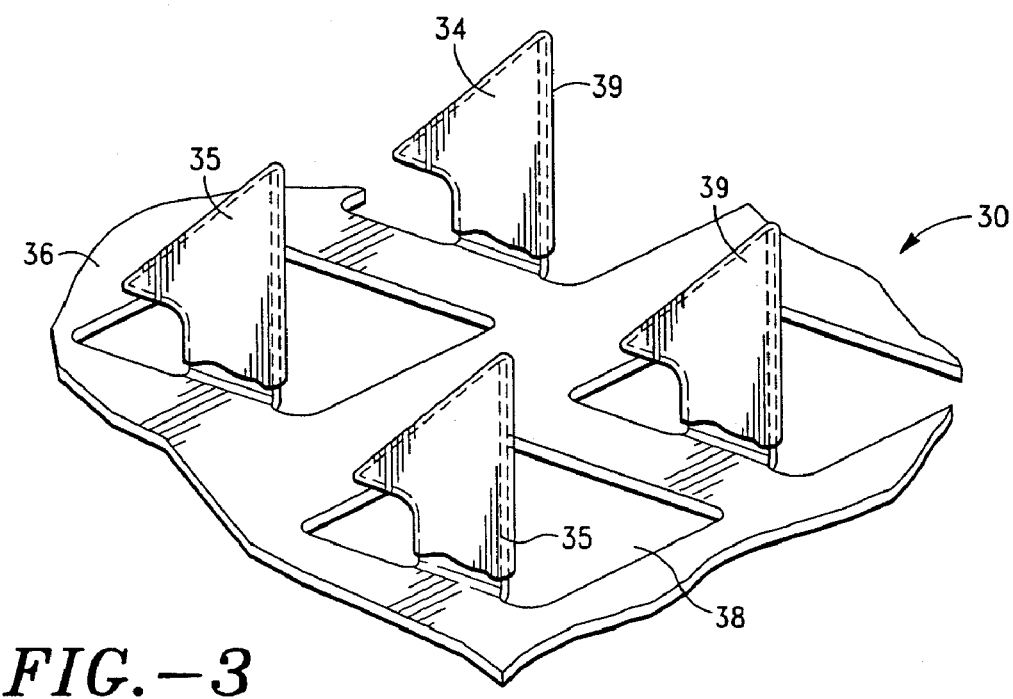
FIG. 3 is a perspective view of the microprojection member shown in FIG. 2 having a coating deposited on the microprojections, according to the invention.

Referring now to FIG. 3, there is shown a microprojection member 30 having microprojections 34 that include a biocompatible coating 35 that includes a PTH-based agent. According to the invention, the coating 35 can partially or completely cover each microprojection 34. For example, the coating 35 can be in a dry pattern coating on the microprojections 34. The coating 35 can also be applied before or after the microprojections 34 are formed.

According to the invention, the coating 35 can be applied to the microprojections 34 by a variety of known methods. Preferably, the coating is only applied to those portions the microprojection member 30 or microprojections 34 that pierce the skin (e.g., tips 39).

One such coating method comprises dip-coating. Dip-coating can be described as a means to coat the microprojections by partially or totally immersing the microprojections 34 into a coating solution. By use of a partial immersion technique, it is possible to limit the coating 35 to only the tips 39 of the microprojections 34.

A further coating method comprises roller coating, which employs a roller coating mechanism that similarly limits the coating 35 to the tips 39 of the microprojections 34. The roller coating method is disclosed in U.S. application Ser. No. 10/099,604 (Pub. No. 2002/0132054), which is incorporated by reference herein in its entirety. As discussed in detail in the noted application, the disclosed roller coating method provides a smooth coating that is not easily dislodged from the microprojections 34 during skin piercing.

According to the invention, the microprojections 34 can further include means adapted to receive and/or enhance the volume of the coating 35, such as apertures (not shown), grooves (not shown), surface irregularities (not shown) or similar modifications, wherein the means provides increased surface area upon which a greater amount of coating can be deposited.

A further coating method that can be employed within the scope of the present invention comprises spray coating. According to the invention, spray coating can encompass formation of an aerosol suspension of the coating composition. In one embodiment, an aerosol suspension having a droplet size of about 10 to 200 picoliters is sprayed onto the microprojections 10 and then dried.

Pattern coating can also be employed to coat the microprojections 34. The pattern coating can be applied using a dispensing system for positioning the deposited liquid onto the microprojection surface. The quantity of the deposited liquid is preferably in the range of 0.1 to 20 nanoliters/microprojection. Examples of suitable precision-metered liquid dispensers are disclosed in U.S. Pat. Nos. 5,916,524; 5,743,960; 5,741,554; and 5,738,728; which are fully incorporated by reference herein.

Microprojection coating formulations or solutions can also be applied using ink jet technology using known solenoid valve dispensers, optional fluid motive means and positioning means which is generally controlled by use of an electric field. Other liquid dispensing technology from the printing industry or similar liquid dispensing technology known in the art can be used for applying the pattern coating of this invention.

Figure 5:
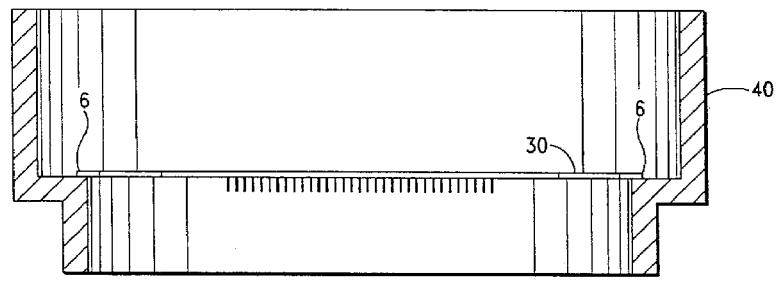
FIG. 5 is a side sectional view of a retainer having a microprojection member disposed therein, according to the invention.
Figure 6:
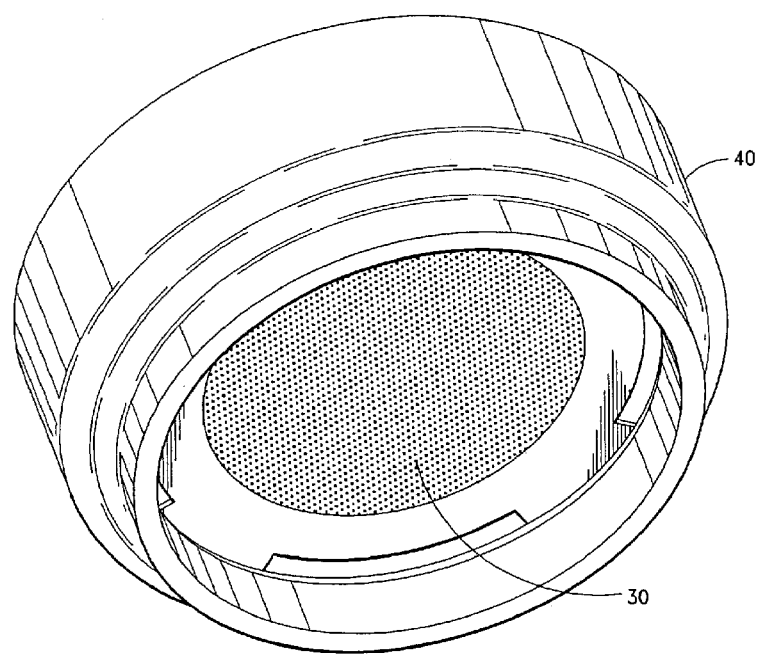
FIG. 6 is a perspective view of the retainer shown in FIG. 4.

Referring now to FIGS. 5 and 6, for storage and application, the microprojection member 30 is preferably suspended in a retainer ring 40 by adhesive tabs 6, as described in detail in U.S. application Ser. No. 09/976,762 (Pub. No. 2002/0091357), which is incorporated by reference herein in its entirety.

Figure 7:
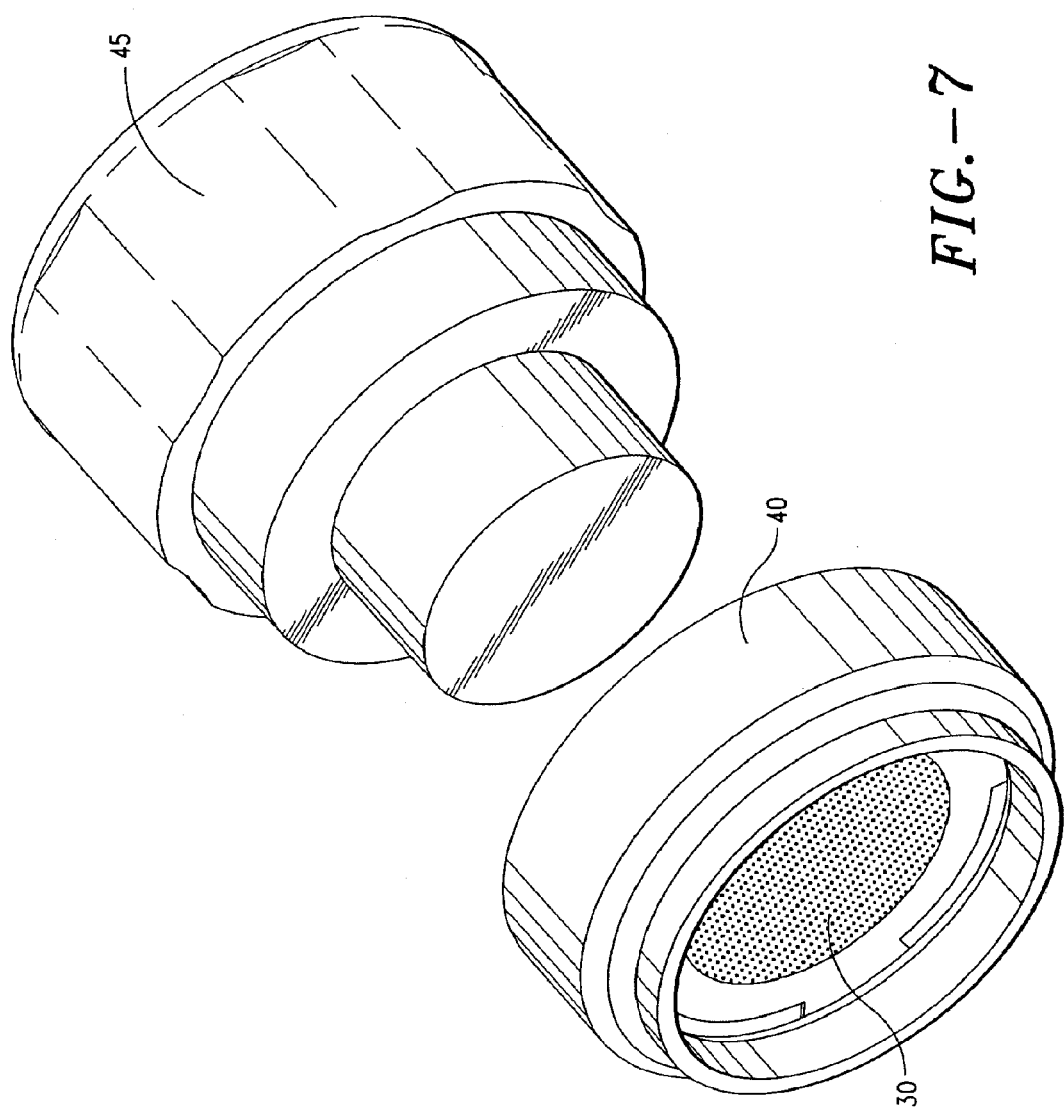
FIG. 7 is an exploded perspective view of an applicator and retainer, according to the invention.

After placement of the microprojection member 30 in the retainer ring 40, the microprojection member 30 is applied to the patient's skin. Preferably, the microprojection member 30 is applied to the patient's skin using an impact applicator 45, such as shown in FIG. 7 and described in Co-Pending U.S. application Ser. No. 09/976,978, which is incorporated by reference herein in its entirety.

As indicated, according to one embodiment of the invention, the coating formulations applied to the microprojection member 30 to form solid biocompatible coatings can comprise aqueous and non-aqueous formulations having at least one PTH-based agent. According to the invention, the PTH-based agent can be dissolved within a biocompatible carrier or suspended within the carrier.

Figure 8:
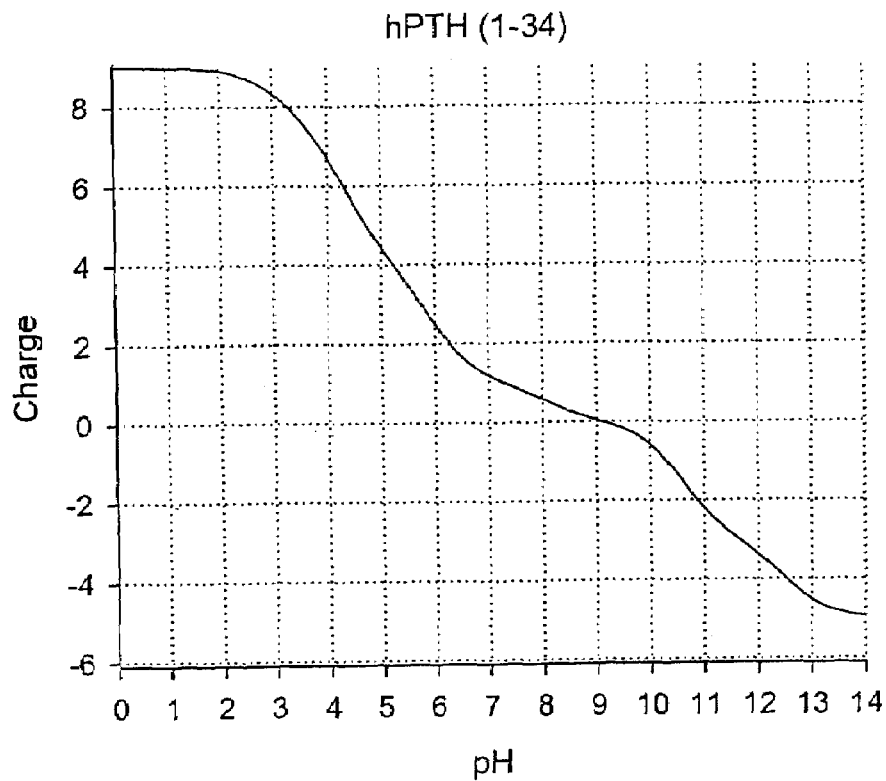
FIG. 8 is a graph illustrating the charge profile for a PTH-based agent, according to the invention.

Referring now to FIG. 8, there is shown the predicted charge profile of hPTH(1-34), a peptide exhibiting 9 acidic pKa's and 5 basic pKa's. As illustrated in FIG. 8, the peptide presents a zero net electric charge at pH 9. This point is also called the isoelectric point or pI.

Figure 9:
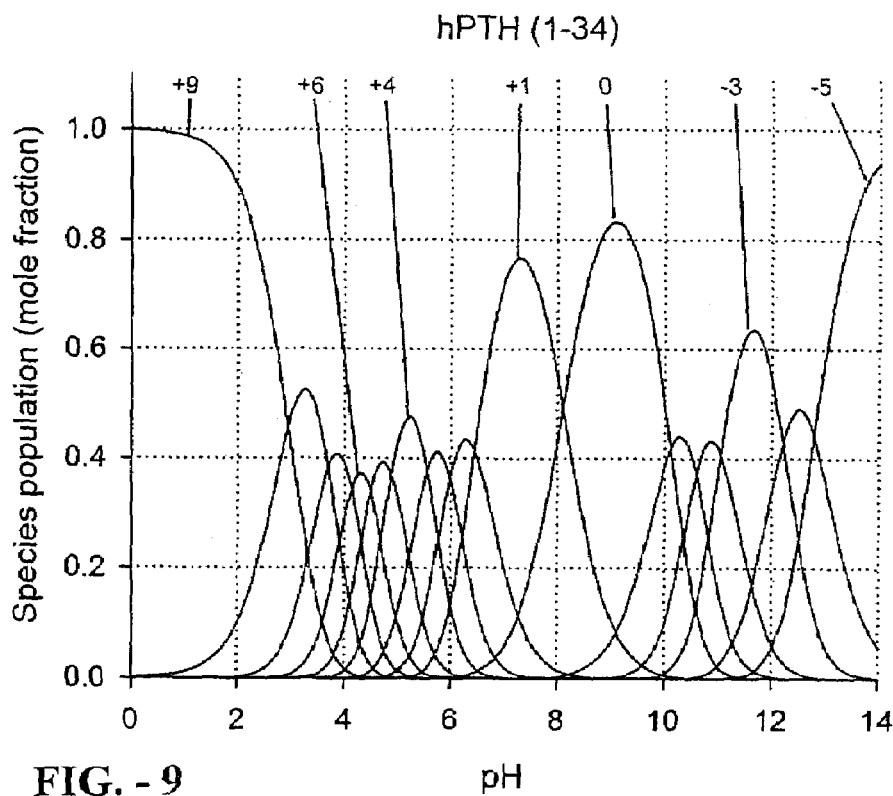
FIG. 9 is a graph illustrating the mole ratios of a net-charged species of a PTH-based agent, according to the invention.

Referring now to FIG. 9, there is shown the predicted mole ratios of the net charged species of hPTH(1-34). As illustrated in FIG. 8, the neutral species only exist in significant amounts in the pH range of pH 6.5 to pH 11.5. In this pH range, the peptide has reduced water solubility and may precipitate out of solution. hPTH and closely related analogs thereof exhibit similar characteristics and behave similarly to hPTH (1-34).

The data thus reflects that hPTH(1-34) solubility that is compatible with formulations acceptable for coating on a microprojection array of the invention can be achieved at a pH below about pH 6 or above pH 11.5. Accordingly, in a preferred embodiment, the pH of the coating formulation is in the range of approximately pH 2-pH 6.

Figure 10:
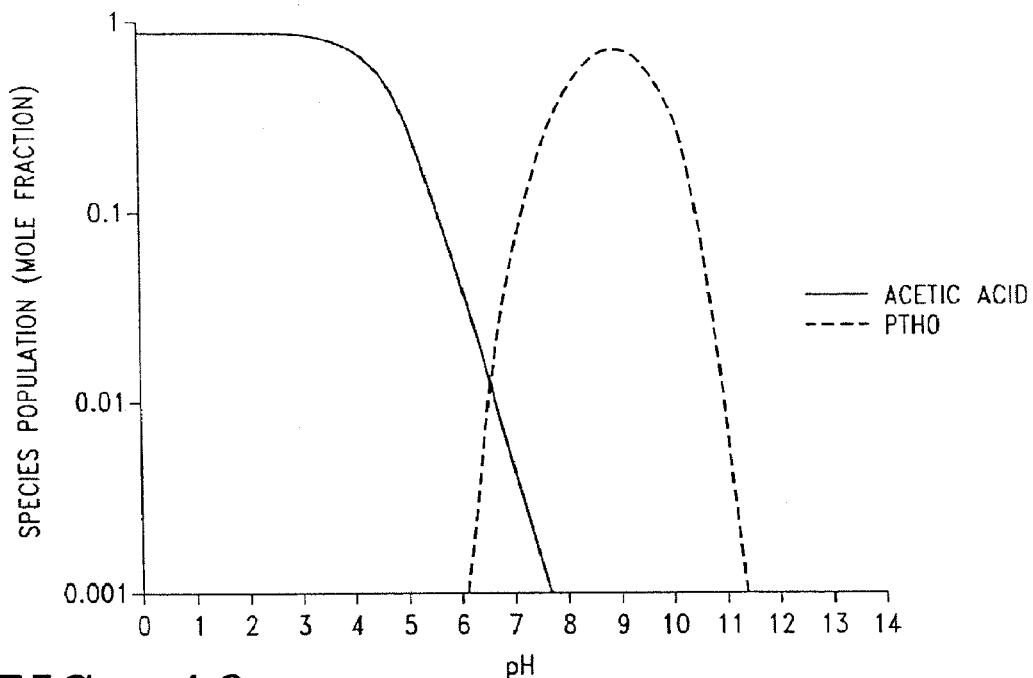
FIG. 10 is a graph illustrating the mole ratios of acetic acid and the neutral form of a PTH-based agent, according to the invention.

Referring now to FIG. 10, there is shown a superposition of the mole ratios for acetic acid and the neutral form of hPTH (1-34). The pH of a PTH hexaacetate (mole ratio 1 to 6) in solution is predicted to be about pH 5. At pH 5, negligible amounts of PTH are present as PTH zero net charge (PTH 0). The PTH is also highly soluble in water at concentrations in excess of 20%. During drying and subsequent storage, the free acetic acid will evaporate inherently resulting in formation of the water insoluble PTH 0. Subsequent reconstitution in water will not allow total solubilization of PTH. Accordingly, the use of a low volatility counterion provides a solid soluble formulation of PTH as long as the pH is maintained at least 2.5 pH units, preferably 3 pH units, below the pI of PTH. Preferably, this can be achieved by providing at least about two low volatility counterions to each molecule of PTH.

Therefore, in one embodiment of the invention, the coating formulations include a counterion or a mixture of counterions. Further, in the preferred pH range of pH 3-pH 6, the PTH-based agent will bear a positive charge.

In a preferred embodiment, the PTH-based agent is selected from the group consisting of hPTH(1-34), hPTH salts and analogs, teriparatide and related peptides, including, recombinant hPTH(1-34), synthetic hPTH(1-34), PTH(1-34), teriparatide, hPTH(1-34) salts, simple derivatives of hPTH(1-34), such as hPTH(1-34) amide, and closely related molecules, such as hPTH(1-33) or hPTH(1-31) amide, and any other closely related osteogenic peptide. Synthetic hPTH (1-34) is the most preferred PTH-based agent.

Examples of suitable hPTH salts include, without limitation, acetate, propionate, butyrate, pentanoate, hexanoate, heptanoate, levulinate, chloride, bromide, citrate, succinate, maleate, glycolate, gluconate, glucuronate, 3-hydroxyisobutyrate, tricarballylicate, malonate, adipate, citraconate, glutarate, itaconate, mesaconate, citramalate, dimethylolpropinate, tiglicate, glycerate, methacrylate, isocrotonate, β-hydroxibutyrate, crotonate, angelate, hydracrylate, ascorbate, aspartate, glutamate, 2-hydroxyisobutyrate, lactate, malate, pyruvate, fumarate, tartarate, nitrate, phosphate, benzene, sulfonate, methane sulfonate, sulfate and sulfonate.

Preferably, the PTH-based agent is present in the coating formulation at a concentration in the range of approximately 1-30 wt. %.

More preferably, the amount of PTH-based agent contained in the biocompatible coating on the microprojection member is in the range of 1-1000 µg, even more preferably, in the range of 10-100 µg.

Preferably, the pH of the coating formulation is below about pH 6. More preferably, the coating formulation has a pH in the range of pH 2-pH 6. Even more preferably, the coating formulation has a pH in the range of approximately pH 3-pH 6.

In certain embodiments of the invention, the viscosity of the coating formulation is enhanced by adding low volatility counterions. In one embodiment, the PTH-based agent has a positive charge at the formulation pH and the viscosity-enhancing counterion comprises an acid having at least two acidic pKas. Suitable acids include, without limitation, maleic acid, malic acid, malonic acid, tartaric acid, adipic acid, citraconic acid, fumaric acid, glutaric acid, itaconic acid, meglutol, mesaconic acid, succinic acid, citramalic acid, tartronic acid, citric acid, tricarballylic acid, ethylenediaminetetraacetic acid, aspartic acid, glutamic acid, carbonic acid, sulfuric acid and phosphoric acid.

Another preferred embodiment is directed to a viscosity-enhancing mixture of counterions, wherein the PTH-based agent has a positive charge at the formulation pH and at least one of the counterions comprises an acid having at least two acidic pKas. The other counterion is an acid with one or more pKas. Examples of suitable acids include, without limitation, hydrochloric acid, hydrobromic acid, nitric acid, sulfuric acid, maleic acid, phosphoric acid, benzene sulfonic acid, methane sulfonic acid, citric acid, succinic acid, glycolic acid, gluconic acid, glucuronic acid, lactic acid, malic acid, pyruvic acid, tartaric acid, tartronic acid, fumaric acid, acetic acid, propionic acid, pentanoic acid, carbonic acid, malonic acid, adipic acid, citraconic acid, levulinic acid, glutaric acid, itaconic acid, meglutol, mesaconic acid, citramalic acid, citric acid, aspartic acid, glutamic acid, tricarballylic acid and ethylenediaminetetraacetic acid.

In the noted embodiments of the invention, the amount of counterion is preferably sufficient to neutralize the charge of the PTH. In such embodiments, the counterion or the mixture of counterion is preferably sufficient to neutralize the charge present on the agent at the pH of the formulation. In additional embodiments, excess counterion (as the free acid or as a salt) is added to the peptide to control pH and provide adequate buffering capacity.

In one preferred embodiment, the agent comprises hPTH (1-34) and the counterion comprises a viscosity-enhancing mixture of counterions chosen from the group consisting of citric acid, tartaric acid, malic acid, hydrochloric acid, glycolic acid and acetic acid. Preferably, the counterions are added to the formulation to achieve a viscosity in the range of about 20-200 cp.

In a preferred embodiment, the viscosity-enhancing counterion comprises an acidic counterion, such as a low volatility weak acid. Preferably, the low volatility weak acid counterion exhibits at least one acidic pKa and a melting point higher than about 50° C. or a boiling point higher than about 170° C. at $P_{atm}$. Examples of such acids include, without limitation, citric acid, succinic acid, glycolic acid, gluconic acid, glucuronic acid, lactic acid, malic acid, pyruvic acid, tartaric acid, tartronic acid and fumaric acid.

In another embodiment, the counterion comprises a strong acid. Preferably, the strong acid exhibits at least one pKa lower than about 2. Examples of such acids include, without limitation, hydrochloric acid, hydrobromic acid, nitric acid, sulfonic acid, sulfuric acid, maleic acid, phosphoric acid, benzene sulfonic acid and methane sulfonic acid.

Another preferred embodiment is directed to a mixture of counterions, wherein at least one of the counterion comprises a strong acid and at least one of the counterions comprises a low volatility weak acid.

Another preferred embodiment is directed to a mixture of counterions, wherein at least one of the counterions comprises a strong acid and at least one of the counterions comprises a weak acid with high volatility. Preferably, the volatile weak acid counterion exhibits at least one pKa higher than about 2 and a melting point lower than about 50° C. or a boiling point lower than about 170° C. at $P_{atm}$. Examples of such acids include, without limitation, acetic acid, propionic acid, pentanoic acid and the like.

The acidic counterion is preferably present in an amount sufficient to neutralize the positive charge present on the PTH-based agent at the pH of the formulation. In additional embodiments, excess counterion (as the free acid or as a salt) is added to control pH and to provide adequate buffering capacity.

In another embodiment of the invention, the coating formulation includes at least one buffer. Examples of such buffers include, without limitation, ascorbic acid, citric acid, succinic acid, glycolic acid, gluconic acid, glucuronic acid, lactic acid, malic acid, pyruvic acid, tartaric acid, tartronic acid, fumaric acid, maleic acid, phosphoric acid, tricarballylic acid, malonic acid, adipic acid, citraconic acid, glutaratic acid, itaconic acid, mesaconic acid, citramalic acid, dimethylolpropionic acid, tiglic acid, glyceric acid, methacrylic acid, isocrotonic acid, β-hydroxybutyric acid, crotonic acid, angelic acid, hydracrylic acid, aspartic acid, glutamic acid, glycine and mixtures thereof.

In one embodiment of the invention, the coating formulation includes at least one antioxidant, which can be sequestering agents, such sodium citrate, citric acid, EDTA (ethylene-dinitrilo-tetraacetic acid) or free radical scavengers such as ascorbic acid, methionine, sodium ascorbate and the like. Presently preferred antioxidants comprise EDTA and methionine.

In the noted embodiments of the invention, the concentration of the antioxidant is in the range of approximately 0.01-20 wt. % of the coating formulation. Preferably the antioxidant is in the range of approximately 0.03-10 wt. % of the coating formulation.

In one embodiment of the invention, the coating formulation includes at least one surfactant, which can be zwitterionic, amphoteric, cationic, anionic, or nonionic, including, without limitation, sodium lauroamphoacetate, sodium dodecyl sulfate (SDS), cetylpyridinium chloride (CPC), dodecyltrimethyl ammonium chloride (TMAC), benzalkonium, chloride, polysorbates, such as Tween 20 and Tween 80, other sorbitan derivatives, such as sorbitan laurate, alkoxylated alcohols, such as laureth-4 and polyoxyethylene castor oil derivatives, such as Cremophor EL®.

In one embodiment of the invention, the concentration of the surfactant is in the range of approximately 0.01-20 wt. % of the coating formulation. Preferably the surfactant is in the range of approximately 0.05-1 wt. % of the coating formulation.

In a further embodiment of the invention, the coating formulation includes at least one polymeric material or polymer that has amphiphilic properties, which can comprise, without limitation, cellulose derivatives, such as hydroxyethylcellulose (HEC), hydroxypropylmethylcellulose (HPMC), hydroxypropycellulose (HPC), methylcellulose (MC), hydroxyethylmethylcellulose (HEMC), or ethylhydroxy-ethylcellulose (EHEC), as well as pluronics.

In one embodiment of the invention, the concentration of the polymer presenting amphiphilic properties in the coating formulation is preferably in the range of approximately 0.01-20 wt. %, more preferably, in the range of approximately 0.03-10 wt. % of the coating formulation.

In another embodiment, the coating formulation includes a hydrophilic polymer selected from the following group: hydroxyethyl starch, carboxymethyl cellulose and salts of, dextran, poly(vinyl alcohol), poly(ethylene oxide), poly(2-hydroxyethylmethacrylate), poly(n-vinyl pyrolidone), polyethylene glycol and mixtures thereof, and like polymers.

In a preferred embodiment, the concentration of the hydrophilic polymer in the coating formulation is in the range of approximately 1-30 wt. %, more preferably, in the range of approximately 1-20 wt. % of the coating formulation.

In another embodiment of the invention, the coating formulation includes a biocompatible carrier, which can comprise, without limitation, human albumin, bioengineered human albumin, polyglutamic acid, polyaspartic acid, polyhistidine, pentosan polysulfate, polyamino acids, sucrose, trehalose, melezitose, raffinose, stachyose, mannitol, and other sugar alcohols.

Preferably, the concentration of the biocompatible carrier in the coating formulation is in the range of approximately 2-70 wt. %, more preferably, in the range of approximately 5-50 wt. % of the coating formulation.

In another embodiment, the coating formulation includes a stabilizing agent, which can comprise, without limitation, a non-reducing sugar, a polysaccharide or a reducing sugar.

Suitable non-reducing sugars for use in the methods and compositions of the invention include, for example, sucrose, trehalose, stachyose, or raffinose.

Suitable polysaccharides for use in the methods and compositions of the invention include, for example, dextran, soluble starch, dextrin, and insulin.

Suitable reducing sugars for use in the methods and compositions of the invention include, for example, monosaccharides such as, for example, apiose, arabinose, lyxose, ribose, xylose, digitoxose, fucose, quercitol, quinovose, rhamnose, allose, altrose, fructose, galactose, glucose, gulose, hamamelose, idose, mannose, tagatose, and the like; and disaccharides such as, for example, primeverose, vicianose, rutinose, scillabiose, cellobiose, gentiobiose, lactose, lactulose, maltose, melibiose, sophorose, and turanose, and the like.

Preferably, the concentration of the stabilizing agent in the coating formulation is at ratio of approximately 0.1-2.0:1 with respect to the PTH-based agent, more preferably, approximately 0.25-1.0:1 with respect to the PTH-based agent.

In another embodiment, the coating formulation includes a vasoconstrictor, which can comprise, without limitation, amidephrine, cafaminol, cyclopentamine, deoxyepinephrine, epinephrine, felypressin, indanazoline, metizoline, midodrine, naphazoline, nordefrin, octodrine, omipressin, oxymethazoline, phenylephrine, phenylethanolamine, phenylpropanolamine, propylhexedrine, pseudoephedrine, tetrahydrozoline, tramazoline, tuaminoheptane, tyrnazoline, vasopressin, xylometazoline and the mixtures thereof. The most preferred vasoconstrictors include epinephrine, naphazoline, tetrahydrozoline indanazoline, metizoline, tramazoline, tymazoline, oxymetazoline and xylometazoline.

As will be appreciated by one having ordinary skill in the art, the addition of a vasoconstrictor to the coating formulations and, hence, solid biocompatible coatings of the invention is particularly useful to prevent bleeding that can occur following application of the microprojection member or array and to prolong the pharmacokinetics of the PTH-based agent through reduction of the blood flow at the application site and reduction of the absorption rate from the skin site into the system circulation.

The concentration of the vasoconstrictor, if employed, is preferably in the range of approximately 0.1 wt. % to 10 wt. % of the coating formulation.

In another embodiment of the invention, the coating formulation includes at least one "pathway patency modulator", which can comprise, without limitation, osmotic agents (e.g., sodium chloride), zwitterionic compounds (e.g., amino acids), and anti-inflammatory agents, such as betamethasone 21-phosphate disodium salt, triamcinolone acetonide 21-disodium phosphate, hydrocortamate hydrochloride, hydrocortisone 21-phosphate disodium salt, methylprednisolone 21-phosphate disodium salt, methylprednisolone 21-succinaate sodium salt, paramethasone disodium phosphate and prednisolone 21-succinate sodium salt, and anticoagulants, such as citric acid, citrate salts (e.g., sodium citrate), dextrin sulfate sodium, aspirin and EDTA.

In yet another embodiment of the invention, the coating formulation includes a solubilising/complexing agent, which can comprise Alpha-Cyclodextrin, Beta-Cyclodextrin, Gamma-Cyclodextrin, glucosyl-alpha-Cyclodextrin, maltosyl-alpha-Cyclodextrin, glucosyl-beta-Cyclodextrin, maltosyl-beta-Cyclodextrin, hydroxypropyl beta-Cyclodextrin, 2-hydroxypropyl-beta-Cyclodextrin, 2-hydroxypropyl-gamma-Cyclodextrin, hydroxyethyl-beta-Cyclodextrin, methyl-beta-Cyclodextrin, sulfobutylether-alpha-Cyclodextrin, sulfobutylether-beta-Cyclodextrin, and sulfobutylether-gamma-Cyclodextrin. Most preferred solubilising/complexing agents are beta-Cyclodextrin, hydroxypropyl beta-Cyclodextrin, 2-hydroxypropyl-beta-Cyclodextrin and sulfobutylether7 beta-Cyclodextrin.

The concentration of the solubilising/complexing agent, if employed, is preferably in the range of approximately 1 wt. % to 20 wt. % of the coating formulation.

In another embodiment of the invention, the coating formulation includes at least one non-aqueous solvent, such as ethanol, isopropanol, methanol, propanol, butanol, propylene glycol, dimethysulfoxide, glycerin, N,N-dimethylformamide and polyethylene glycol 400. Preferably, the non-aqueous solvent is present in the coating formulation in the range of approximately 1 wt. % to 50 wt. % of the coating formulation.

Other known formulation adjuvants can also be added to the coating formulations provided they do not adversely affect the necessary solubility and viscosity characteristics of the coating formulation and the physical integrity of the dried coating.

Preferably, the coating formulations have a viscosity less than approximately 500 centipoise and greater than 3 centipoise.

In one embodiment of the invention, the thickness of the biocompatible coating is less than 25 microns, more preferably, less than 10 microns, as measured from the microprojection surface.

The desired coating thickness is dependent upon several factors, including the required dosage and, hence, coating thickness necessary to deliver the dosage, the density of the microprojections per unit area of the sheet, the viscosity and concentration of the coating composition and the coating method chosen.

In accordance with one embodiment of the invention, the method for delivering a PTH-based agent contained in the biocompatible coating on the microprojection member includes the following steps: the coated microprojection member is initially applied to the patient's skin via an actuator, wherein the microprojections pierce the stratum corneum. The coated microprojection member is preferably left on the skin for a period lasting from 5 seconds to 24 hours. Following the desired wearing time, the microprojection member is removed.

Preferably, the amount of PTH-based agent contained in the biocompatible coating (i.e., dose) is in the range of approximately 1 μg-1000 μg, more preferably, in the range of approximately 10-200 μg per dosage unit. Even more preferably, the amount of PTH-based agent contained in the biocompatible coating is in the range of approximately 10-100 μg per dosage unit.

As stated, according to the invention, the PTH-based agent is delivered to the patient in a pulsatile fashion and, hence, exhibit pharmacokinetics resulting in a pulsatile concentration profile. In one embodiment of the invention, the pulsatile concentration profile is reflected (or evidenced) by a curve of PTH-based agent concentration in the host's blood serum versus time having an area under the curve (AUC) in the range of approximately 0.014-5.24 h·ng/mL and a $C_{max}$ in the range of approximately 0.13-0.72 ng/mL for a microprojection member nominally containing 30 μg PTH(1-34).

In a further embodiment of the invention, the pulsatile concentration profile is reflected (or evidenced) by a curve of PTH-based agent concentration in the host's blood serum versus time having an area under the curve (AUC) in the range of approximately 0.014-5.24 h·ng/mL, $C_{max}$ in the range of approximately 0.13-0.72 ng/mL and $T_{max}$ in the range of 5-15 min. for a microprojection member nominally containing 30 μg PTH(1-34).

In a presently preferred embodiment, a 20 μg bolus dose of a PTH-based agent is delivered in a pulsatile fashion by leaving the microprojection member in place for 15 minutes or less.

The noted pulsatile concentration profiles are preferably achieved via a PTH delivery regime in the range of 0.5 (i.e., once every other day)—2 pulses per day, more preferably, one full pulse (or dose) per day. However, as will be appreciated by one having ordinary skill in the art, the PTH can also be delivered via various additional dosing regimes.

In all cases, after a coating has been applied, the coating formulation is dried onto the microprojections 34 by various means. In a preferred embodiment of the invention, the coated microprojection member 30 is dried in ambient room conditions. However, various temperatures and humidity levels can be used to dry the coating formulation onto the microprojections. Additionally, the coated member can be heated, lyophilized, freeze dried or similar techniques used to remove the water from the coating.

It will be appreciated by one having ordinary skill in the art that in order to facilitate drug transport across the skin barrier, the present invention can also be employed in conjunction with a wide variety of iontophoresis or electrotransport systems, as the invention is not limited in any way in this regard. Illustrative electrotransport drug delivery systems are disclosed in U.S. Pat. Nos. 5,147,296, 5,080,646, 5,169,382 and 5,169,383, the disclosures of which are incorporated by reference herein in their entirety.

The term "electrotransport" refers, in general, to the passage of a beneficial agent, e.g., a drug or drug precursor, through a body surface such as skin, mucous membranes, nails, and the like. The transport of the agent is induced or enhanced by the application of an electrical potential, which results in the application of electric current, which delivers or enhances delivery of the agent, or, for "reverse" electrotransport, samples or enhances sampling of the agent. The electrotransport of the agents into or out of the human body may by achieved in various manners.

One widely used electrotransport process, iontophoresis, involves the electrically induced transport of charged ions. Electroosmosis, another type of electrotransport process involved in the transdermal transport of uncharged or neutrally charged molecules (e.g., transdermal sampling of glucose), involves the movement of a solvent with the agent through a membrane under the influence of an electric field. Electroporation, still another type of electrotransport, involves the passage of an agent through pores formed by applying an electrical pulse, a high voltage pulse, to a membrane.

In many instances, more than one of the noted processes may be occurring simultaneously to different extents. Accordingly, the term "electrotransport" is given herein its broadest possible interpretation, to include the electrically induced or enhanced transport of at least one charged or uncharged agent, or mixtures thereof, regardless of the specific mechanism(s) by which the agent is actually being transported. Additionally, other transport enhancing methods, such as sonophoresis or piezoelectric devices, can be used in conjunction with the invention.

EXAMPLES

The following examples are given to enable those skilled in the art to more clearly understand and practice the present invention. They should not be considered as limiting the scope of the invention, but merely as being illustrated as representative thereof.

Example 1

Delivery of hPTH (1-34) from coated microprojection arrays was evaluated in a hairless guinea pig (HGP) model. Microprojection arrays were produced using photo/chemical etching, and forming. The microprojection arrays used in this study were 2 cm$^2$ in area, with 320 microprojections/cm$^2$ and a projection length of 200 μm.

The microprojection arrays were coated with a 25% aqueous solution of hPTH (1-34) at 40±10 μg per 2 cm$^2$ array, with a solid coating limited to the first 100 μm of the microprojections. Each coated microprojection array was assembled to a flexible polymeric adhesive backing. The resulting patch was assembled onto a retainer ring and loaded on a reusable impact applicator at the time of application to the HGP.

Each anesthetized HGP received a patch that was applied to a clean skin area for a wearing time of 1 hour. At various time intervals following patch application, blood samples were taken. Plasma hPTH (1-34) levels were determined using an enzyme immunoassay (Peninsula Lab).

Figure 11:
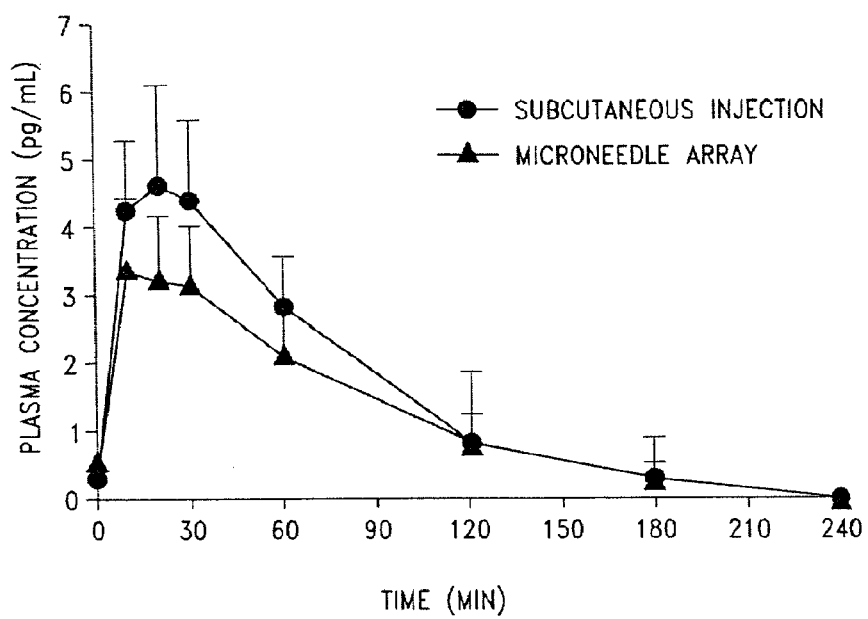
FIG. 11 is a graph comparing plasma concentration of a PTH-based agent following transdermal and subcutaneous delivery, according to the invention.

The plasma levels of HGPs receiving microprojection array patches coated with 40 μg of hPTH (1-34) were compared with subcutaneous (SC) administration of 20 μg of hPTH (1-34) (see FIG. 11).

An intravenous (IV) injection of 23 μg hPTH (1-34) was also performed in a separate group of 5 animals and the area under the curve (AUC) was used as a reference to calculate the total amounts absorbed/delivered following SC or microneedle array administration. The pharmacokinetic parameters of hPTH (1-34) following IV, SC, and microneedle array administration are shown in Table 1.

The pharmacokinetic (PK) profiles of immunoreactive hPTH(1-34) were similar for both SC and microprojection array delivery; $t_{max}$ (SC: 10 min vs 20 min, $C_{max}$ (SC: 4.6±1.5 ng/mL vs 3.4±1.0 ng/ml); AUC$_{240\ min}$ (SC: 8.2±2.9 μg vs 6.6±1.8 μg) (n=10 per group, mean±SD).

The data indicate that hPTH(1-34) can be transdermally delivered with a PK profile similar to that of subcutaneous injection and highlight the feasibility of transdermal delivery of hPTH(1-34) using a microprojection array technology, which could be a more convenient alternative for osteoporotic patients.

TABLE 1

| Route of Administration | IV | SC | Array |
|---|---|---|---|
| Single Dose Parameters | | | |
| Dose Amount (μg) | 22.5 | 19.5 | 40.0 |
| Dosage (μg/kg) | 30.9 | 29.2 | 52.8 |
| Fraction dose absorbed/delivered (%) | 100 | 42 | 17 |
| C$_{max}$ (ng/mL) | 71.2 +/− 11.2 | 4.6 +/− 1.5 | 3.4 +/− 1.0 |
| T$_{max}$ (min) | 1 | 20 | 10 |
| AUC (ng*h/ml) | 13.2 +/− 3.8 | 5.4 +/− 1.7 | 3.9 +/− 1.1 |
| Dose absorbed/delivered (μg) | | 8.2 +/− 2.9 | 6.6 +/− 1.8 |

Example 2

Example 2 demonstrates the utilization of a weak acid with a hPTH (1-34) agent to enhance the viscosity. The interaction of the weak acid anion with the positively charged a hPTH (1-34) agent leads to the formation of secondary bonds, e.g. hydrogen bonds, which results in an increase in solution viscosity. The greater the number of acidic groups, the greater the number of secondary bonds formed between the anions and the hPTH (1-34) agent, hence the greater the viscosity increase. Thus, the theoretical viscosity enhancing capabilities increase when monoacids, di-acids, tri-acids and tetra-acids are compared.

Various weak acid buffers have been incorporated in the hPTH (1-34) formulations in this experiment. A control formulation including PTH (1-34) actate with sucrose was also prepared. The experiment investigated the physicochemical properties afforded to hPTH (1-34) by various mixtures of mono-, di- and tri-acids and the stability of the solution formulations over a 48 hr period at 2-8° C. The PTH (1-34) formulations were buffered to a pH 5.2.

Referring now to Table 2, there is shown the viscosity results of the formulations. The citric and malic acid buffered formulations exhibited the largest increase viscosity enhancement compared to the control formulation (Lot No. 7528069A). Citric acid, a tri-acid, yielded a formulation with the highest viscosity.

The data reflected in Table 2 demonstrates that counterion mixtures of citric acid/acetic acid, malic acid/acetic acid, tartaric acid/acetic acid and hydrochloric acid/acetic acid increase the viscosity of hPTH (1-34) with respect to the control formulation of 20% PTH, 20% Sucrose, 0.2% Tween 20. Based on the results reflected in Table 2, the trend for viscosity enhancement following addition of weak acid buffers is preferably tri-acid to di-acid to mono-acid.

TABLE 2

| Formulation Lot No. | Viscosity (cP) |
|---|---|
| 20% PTH, 20% Sucrose, 0.2% Tween 20 | 68 |
| 20% PTH, 20% Sucrose, 0.5% HCl, 0.2% Tween 20 | 87 |
| 20% PTH, 20% Sucrose, 1.2% glycolic acid, 0.2% Tween 20 | 53 |
| 20% PTH, 20% Sucrose, 1.4% malic acid, 0.2% Tween 20 | 116 |
| 20% PTH, 20% Sucrose, 1.2% tartaric acid, 0.2% Tween 20 | 77 |
| 20% PTH, 20% Sucrose, 1.7% citric acid, 0.2% Tween 20 | 172 |

Example 3

Example 3 demonstrates the utilization of a mixture of counterions with a hPTH(1-34) agent to enhance the dissolution of hPTH-based agent in vivo.

In a solid coating on a microprojection array, the agent is typically present in an amount of less than about 1 mg per unit dose. With the addition of excipients and counterions, the total mass of solid coating can be less than 3 mg per unit dose.

The array is usually present on an adhesive backing, which is attached to a disposable polymeric retainer ring. This assembly is typically packaged individually in a pouch or a polymeric housing. In addition to the assembly, this package contains an atmosphere (usually inert) that represents a volume of at least 3 mL. This large volume (as compared to that of the coating) acts as a sink for any volatile component. For example, at 20° C., the amount of acetic acid present in a 3 mL atmosphere as a result of its vapor pressure would be about 0.15 mg. This amount is typically what would be present in the solid coating if acetic acid were used as a counterion. In addition, components of the assembly, such as the adhesive, are likely to act as additional sinks for volatile components. As a result, during long-term storage, it is likely that the concentration of any volatile component present in the coating would change dramatically. These conditions are typical of packaging of pharmaceutical compounds where large amounts of excipients are usually present. Even with very potent biotechnology compounds that are lyophilized for use as an injectable, a very large excess of buffers and excipients is present in the dry cake.

In solution, or in the solid state, volatilization of the counterion occurs at the interface between the solution or the solid and the atmosphere. High diffusivity of solutes generally minimizes differences in concentration between the interface and the bulk of the solution. Conversely, in a solid state, diffusivity is very slow and greater concentration gradients of the volatile counterion are achieved between the interface and the bulk of the solution. Ultimately, the outer layer of the coating is depleted in counterion while the bulk of the solid coating is relatively unchanged, as compared to the initial dry state. This situation can result in a highly insoluble outer coating if the counterion is associated with an agent that is substantially insoluble in its neutral net charge state. Indeed, volatilization of the counterion results in formation of the water insoluble neutral species. This, in turn, jeopardizes dissolution of the agent from the solid coating upon exposure to the biological fluids. Accordingly, this experiment investigated the effect of adding low volatility counterions to improve coating solubility.

Several aqueous formulations containing hPTH (1-34) were prepared and are set forth in Table 3. These formulations contained the volatile counterion acetic acid. Certain formulations contained additional low volatility counterions hydrochloric acid, glycolic acid, or tartaric acid. The microprojection arrays (microprojection length 200 mm, 595 microprojections per array) had a skin contact area of approximately 2 cm$^2$. The tips of the microprojections were coated with the noted formulations by passing the arrays over a rotating drum carrying the PTH formulations, using the method and apparatus disclosed in U.S. patent application Ser. No. 10/099,604, which is hereby incorporated by reference herein.

Four successive coatings were performed on each microprojection array at a temperature of 2-8° C. The amount of peptide coated on the arrays was evaluated by ultraviolet spectroscopy at a wavelength of 275 nm. Scanning electron microscopy revealed that the solid coating had a very smooth surface with no evidence of cracking. Furthermore, good uniformity of coating from microprojection to microprojection was observed, with the coating limited to the first 100 µm of the microprojection tip.

Tip-coated arrays prepared in this manner were subsequently used for drug delivery studies in hairless guinea pigs (HGPs). HGPs were anesthetized by intramuscular injection of xylazine (8 mg/kg) and ketamine HCl (44 mg/kg). Anesthetized HGPs were catheterized through the carotid artery. The catheter was flushed with heparinized saline (20 IU/mL) to prevent clotting. The HGPs were maintained under anesthesia throughout the experiment via injection of sodium pentobarbital (32 mg/mL) directly into the catheter (0.1 mL/injection). Before application, blood samples were taken into heparinized vials (final concentration of heparin at 15 IU/mL), which served as 0 or baseline samples.

The application of the coated microprojection arrays was performed on the flank of the anesthetized animals with a spring-driven impact applicator (total energy=0.4 Joules, delivered in less than 10 milliseconds), of the type disclosed in U.S. patent application Ser. No. 09/976,798, which is hereby incorporated in its entirety by reference herein. The system applied comprised a coated microprojection array device, adhered to the center of a LDPE backing with an adhesive (7 cm2 disc). Patches were retained on the skin for 1 h (n=4-5). A control group of animals (n=5) received an intravenous injection of 22 µg hPTH.

Blood samples were collected through the carotid catheter at time intervals following patch application. All blood samples were centrifuged immediately for plasma collection, the latter was then stored at −80° C. until analysis. Plasma hPTH was determined by the EIA, a commercial enzyme immunoassay kit for hPTH from Peninsula Lab. (San Carlos, Calif.). The hPTH dose delivered by microprojection arrays was extrapolated based on the area under the curve (AUC) calculation compared to IV administration of hPTH.

As shown in Table 3, different amounts of PTH were delivered from each solid formulation. The solid formulations containing only PTH acetate delivered less than 2 mg on average. Addition of low volatility counterions to PTH acetate increased delivery significantly to up to 11.2 mg after the addition of the low volatility counterion glycolic acid. The two other non-counterions tested, i.e., tartaric and hydrochloric acid, also increased PTH delivery. Specifically, the counterion mixtures of glycolic acid/acetic acid, tartaric acid/acetic acid and hydrochloric acid/acetic acid increased the delivered amount of hPTH (1-34) with respect to the control formulation of 21.2% PTH, 3.8% acetic acid.

size exclusion chromatography (SEC), respectively. The results for each formulation are summarized in Tables 5-14.

Figure 12:
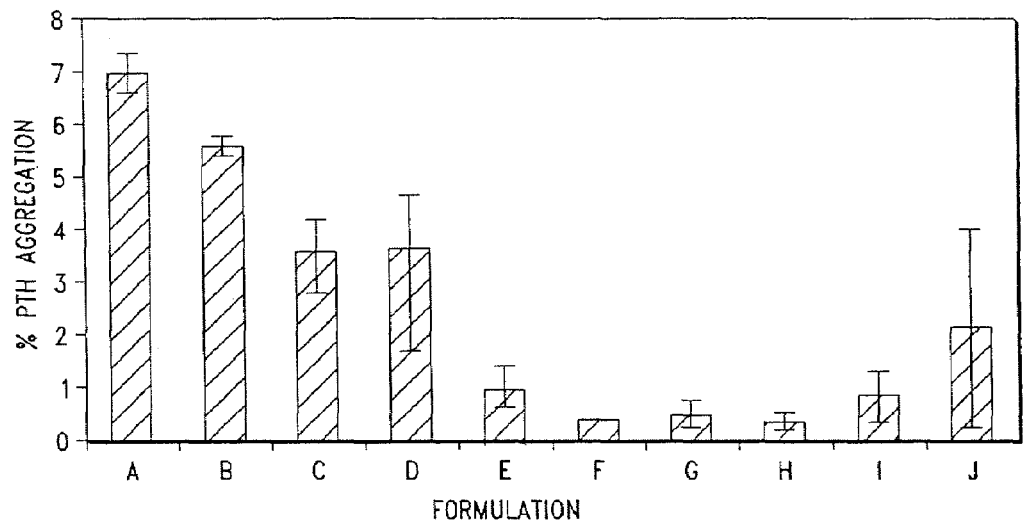
FIG. 12 is a graph illustrating the aggregation percentage of a PTH-based agent with and without sucrose as a stabilizer, according to the invention.

The stability data generated suggests that the main mechanism of degradation of PTH in the solid state is via an aggregation process. Furthermore, the stability data indicates that addition of sucrose prevents aggregation of hPTH (1-34). FIG. 12 shows the percent aggregation of hPTH (1-34) formulations with and without sucrose at the 60-day time point.

TABLE 4

| Formulation | Formulation Composition (% w/w) |
|---|---|
| A | 20% PTH, 12.7% HCl |
| B | 20% PTH, 12.7% HCl, 0.01% EDTA |
| C | 20% PTH, 12.7% HCl, 1% methionine, 0.01% EDTA |
| D | 20% PTH, 12.7% HCl, 1.2% Tartaric acid, 1% methionine, 0.2% Tween 20, 0.01% EDTA |
| E | 20% PTH, 20% sucrose, 12.7% HCl, 0.2% Tween 20 |
| F | 20% PTH, 20% sucrose, 12.7% HCl, 0.2% Tween 20, 0.03% EDTA |

TABLE 3

| Formulation solution (wt %) | Ratio (PTH:Acetate:low volatility counterion) | Amount of PTH coated on array (μg) ± SD | Amount delivered (μg) ± SD |
|---|---|---|---|
| 21.2% PTH, 3.8% acetic acid, water (q.s.) | 1:3:0 | 28.0 ± 6.6 | 1.1 ± 1.1 |
| 21.2% PTH, 3.8% acetic acid, water | 1:3:0 | 35.0 ± 11.4 | 1.5 ± 1.7 |
| 22.3% PTH, 2.7% acetic acid, 0.4% HCl, water | 1:2:2 | 40.0 ± 9.8 | 5.9 ± 2.5 |
| 16.2% PTH, 3.8% acetic acid, 0.5% HCl, 20.2% excipients, water. | 1:3:3 | 30.5 ± 2.3 | 6.1 ± 4.0 |
| 6.2% PTH, 3.8% acetic acid, 2.1% glycolic acid, 12.2% excipients, water. | 1:3:4 | 45.9 ± 11.7 | 11.2 ± 2.7 |
| 16.2% PTH, 3.8% acetic acid, 1.2% Tartaric acid, 20.23% excipients, water | 1:3:2 | 29.0 ± 4.3 | 4.2 ± 1.5 |

Example 4

Example 4 demonstrates the utilization of a stabilizing agent with a hPTH(1-34) agent to enhance the stability of the hPTH(1-34) agent.

Ten formulations, as shown in Table 4, were coated on titanium and monitored for chemical stability at 40° C. for a period of 60 days. The pH of the formulations containing the weak acid buffers was approximately pH 5.2, while the pH of the chloride containing formulations was approximately pH 5.4. The purity, oxidized PTH (1-34) product and soluble aggregates were monitored as a function of time by reverse phase high-pressure liquid chromatography (RPHPLC) and TABLE 4-continued

| Formulation | Formulation Composition (% w/w) |
|---|---|
| G | 20% PTH, 20% sucrose, 12.7% HCl, 2% methionine, 0.2% Tween 20, 0.03% EDTA |
| H | 20% PTH, 20% sucrose, 1.2% Tartaric acid, 2% methionine, 0.2% Tween 20, 0.03% EDTA |
| I | 20% PTH, 20% sucrose, 1.2% Glycolic acid, 2% methionine, 0.2% Tween 20, 0.03% EDTA |
| J | 20% PTH, 20% sucrose, 1.7% Citric acid, 2% methionine, 0.2% Tween 20, 0.03% EDTA |

TABLE 5

Formulation Composition: 20% PTH, 12.7% HCL

| | RP-HPLC | | | | SEC | |
|---|---|---|---|---|---|---|
| Time (Days) | PTH Purity [%] (% RSD) | Total oxid [%] (% RSD) | Isomer [%] (% RSD) | Unknown[%] (% RSD) | Aggregation [%] (% RSD) | Unknown [%] |
| 0 | 93.91 (0.41) | 0.22 (7.87) | 4.40 (1.25) | 1.47 (22.55) | 0.10 (5.59) | 0.00 |
| 10 | 92.55 (0.82) | 0.27 (7.62) | 4.39 (0.88) | 2.79 (27.97) | 2.27 (66.38) | 0.39 |
| 24 | 89.76 (1.09) | 0.39 (12.76) | 4.45 (0.91) | 5.41 (18.04) | 4.73 (31.30) | 1.13 |
| 60 | 85.94 (0.47) | 0.38 (9.16) | 4.19 (1.18) | 9.49 (4.39) | 6.93 (5.34) | 3.22 |

TABLE 6

Formulation Composition: 20% PTH, 12.7% HCL, 0.01% EDTA

| | RP-HPLC | | | SEC | |
|---|---|---|---|---|---|
| Time (Days) | PTH Purity [%] (% RSD) | Total oxid [%] (% RSD) | Isomer [%] (% RSD) | Unknown [%] (% RSD) | Aggregation [%] (% RSD) | Unknown [%] |
| 0 | 93.75 (0.13) | 0.21 (7.39) | 4.33 (1.44) | 1.71 (5.00) | 0.15 (14.19) | 0.00 |
| 10 | 93.04 (0.19) | 0.25 (4.00) | 4.22 (0.96) | 2.48 (7.04) | 1.59 (15.78) | 0.12 |
| 24 | 91.51 (0.68) | 0.36 (13.89) | 4.41 (2.16) | 3.72 (15.63) | 2.66 (30.89) | 0.52 |
| 60 | 87.82 (0.70) | 0.37 (3.15) | 4.04 (3.73) | 7.77 (6.35) | 5.54 (3.62) | 1.97 |

TABLE 7

Formulation Composition: 20% PTH, 12.7% HCl, 0.01% EDTA, 1% Methionine

| | RP-HPLC | | | SEC | |
|---|---|---|---|---|---|
| Time (Days) | PTH Purity [%] (% RSD) | Total oxid [%] (% RSD) | Isomer [%] (% RSD) | Unknown [%] (% RSD) | Aggregation [%] (% RSD) | Unknown [%] |
| 0 | 93.77 (0.14) | 0.19 (2.99) | 4.29 (1.66) | 1.75 (3.73) | 0.14 (7.14) | 0.00 |
| 10 | 92.83 (0.59) | 0.51 (9.93) | 4.34 (1.80) | 2.32 (20.92) | 2.15 (44.83) | 0.32 |
| 24 | 90.69 (0.49) | 0.36 (18.73) | 4.46 (0.69) | 4.49 (9.64) | 3.01 (37.35) | 0.47 |
| 60 | 90.34 (0.71) | 0.36 (6.93) | 4.36 (10.62) | 4.94 (16.60) | 3.53 (20.6) | 0.79 |

TABLE 8

Formulation Composition: 20% PTH, 20% Sucrose, 12.7% HCl, 0.2% Tween20, 0.03% EDTA

| | RP-HPLC | | | SEC | |
|---|---|---|---|---|---|
| Time (Days) | PTH Purity [%] (% RSD) | Total oxid [%] (% RSD) | Isomer [%] (% RSD) | Unknown [%] (% RSD) | Aggregation [%] (% RSD) | Unknown [%] |
| 0 | 93.99 (0.38) | 0.45 (2.59) | 4.21 (1.35) | 1.26 (18.38) | 0.12 (12.39) | 0.00 |
| 10 | 92.98 (0.68) | 0.40 (28.67) | 4.25 (0.76) | 2.38 (30.89) | 0.40 (98.97) | 0.01 |
| 24 | 92.41 (0.06) | 0.54 (6.68) | 4.54 (0.34) | 2.51 (1.79) | 0.25 (10.58) | 0.00 |
| 60 | 91.88 (0.37) | 0.57 (1.75) | 4.24 (1.43) | 3.31 (8.41) | 0.88 (60.36) | 0.00 |

TABLE 9

Formulation Composition: 20% PTH, 1.2% Tartaric acid, 0.01% EDTA, 1% Methionine, 0.2% Tween20

| | RP-HPLC | | | SEC | |
|---|---|---|---|---|---|
| Time (Days) | PTH Purity [%] (% RSD) | Total oxid [%] (% RSD) | Isomer [%] (% RSD) | Unknown [%] (% RSD) | Aggregation [%] (% RSD) | Unknown [%] |
| 0 | 93.79 (0.36) | 0.44 (11.53) | 4.30 (0.48) | 1.47 (18.95) | 0.13 (20.35) | 0.00 |
| 10 | 93.50 (0.08) | 0.34 (3.36) | 4.35 (1.09) | 1.81 (2.84) | 0.62 (131.08) | 0.01 |
| 24 | 91.40 (2.04) | 0.67 (7.90) | 4.34 (0.53) | 3.60 (53.01) | 2.10 (88.57) | 0.08 |
| 60 | 90.40 (0.03) | 0.66 (10.04) | 3.99 (2.75) | 4.95 (0.77) | 3.59 (28.55) | 0.33 |

TABLE 10

Formulation Composition: 20% PTH, 20% Sucrose, 12.7% HCl, 0.2% Tween20, 0.03% EDTA, 2% Methionine

| | RP-HPLC | | | SEC | |
|---|---|---|---|---|---|
| Time (Days) | PTH Purity [%] (% RSD) | Total oxid [%] (% RSD) | Isomer [%] (% RSD) | Unknown [%] (% RSD) | Aggregation [%] (% RSD) | Unknown [%] |
| 0 | 93.92 (0.35) | 0.36 (3.24) | 4.10 (3.51) | 1.63 (10.64) | 0.15 (10.41) | 0.00 |
| 10 | 93.19 (0.67) | 0.36 (1.59) | 4.32 (1.67) | 2.13 (26.75) | 0.53 (106.67) | 0.03 |
| 24 | 92.66 (0.38) | 0.40 (15.94) | 4.55 (3.58) | 2.39 (8.32) | 0.26 (3.85) | 0.02 |
| 60 | 92.64 (0.17) | 0.39 (15.80) | 4.31 (3.04) | 2.66 (5.22) | 0.49 (48.12) | 0.02 |

TABLE 11

Formulation Composition: 20% PTH, 20% Sucrose, 1.2% Tartaric acid, 0.2% Tween20, 0.03% EDTA, 2% methionine

| Time (Days) | RP-HPLC | | | | SEC | |
|---|---|---|---|---|---|---|
| | PTH Purity [%] (% RSD) | Total oxid [%] (% RSD) | Isomer [%] (% RSD) | Unknown [%] (% RSD) | Aggregation [%] (% RSD) | Unknown[%] |
| 0 | 93.48 (0.12) | 0.35 (11.44) | 4.40 (0.47) | 1.77 (5.35) | 0.12 (9.90) | 0.01 |
| 10 | 93.50 (0.08) | 0.34 (3.36) | 4.35 (1.09) | 1.81 (2.84) | 0.62 (131.08) | 0.01 |
| 24 | 92.40 (0.44) | 0.37 (14.30) | 4.65 (2.28) | 2.58 (10.62) | 0.34 (37.00) | 0.01 |
| 60 | 91.83 (0.06) | 0.41 (5.12) | 4.49 (1.48) | 3.28 (2.13) | 0.36 (29.72) | 0.01 |

TABLE 12

Formulation Composition: 20% PTH, 20% Sucrose, 12.7% HCl, 0.2% Tween20

| Time (Days) | RP-HPLC | | | | SEC | |
|---|---|---|---|---|---|---|
| | PTH Purity [%] (% RSD) | Total oxid [%] (% RSD) | Isomer [%] (% RSD) | Unknown [%] (% RSD) | Aggregation [%] (% RSD) | Unknown [%] |
| 0 | 93.76 (0.28) | 0.44 (2.27) | 4.20 (0.86) | 1.60 (13.80) | 0.14 (4.03) | 0.00 |
| 10 | 92.94 (0.29) | 0.29 (39.16) | 4.21 (1.58) | 2.56 (10.80) | 0.23 (26.45) | 0.00 |
| 24 | 92.58 (0.12) | 0.45 (3.14) | 4.61 (0.92) | 2.36 (5.99) | 0.51 (46.21) | 0.00 |
| 60 | 92.31 (0.05) | 0.47 (3.01) | 4.19 (1.69) | 3.03 (1.40) | 0.38 (11.16) | 0.00 |

TABLE 13

Formulation Composition: 20% PTH, 20% Sucrose, 1.2% Glycolic acid, 0.2% Tween 20, 0.03% EDTA, 2% Methionine

| Time (Days) | RP-HPLC | | | | SEC | |
|---|---|---|---|---|---|---|
| | PTH Purity [%] (% RSD) | Total oxid [%] (% RSD) | Isomer [%] (% RSD) | Unknown [%] (% RSD) | Aggregation [%] (% RSD) | Unknown [%] |
| 0 | 93.56 (0.12) | 0.40 (3.79) | 4.29 (1.08) | 1.74 (4.78) | 0.15 (13.33) | 0.00 |
| 10 | 93.41 (0.34) | 0.42 (8.43) | 4.28 (0.89) | 1.90 (16.54) | 0.37 (15.51) | 0.00 |
| 24 | 91.95 (0.90) | 0.51 (6.03) | 4.63 (1.14) | 2.92 (25.52) | 0.48 (42.42) | 0.00 |
| 60 | 91.85 (0.54) | 0.42 (2.73) | 4.47 (3.02) | 3.25 (16.05) | 0.82 (56.11) | 0.01 |

TABLE 14

Formulation Composition: 20% PTH, 20% Sucrose, 1.7% Citric acid, 0.2% Tween20, 0.03% EDTA, 2% Methionine

| Time (Days) | RP-HPLC | | | | SEC | |
|---|---|---|---|---|---|---|
| | PTH Purity [%] (% RSD) | Total oxid [%] (% RSD) | Isomer [%] (% RSD) | Unknown [%] (% RSD) | Aggregation [%] (% RSD) | Unknown [%] |
| 0 | 93.71 (0.34) | 0.37 (3.15) | 4.22 (1.54) | 1.70 (15.28) | 0.11 (10.19) | 0.00 |
| 10 | 93.63 (0.11) | 0.38 (14.65) | 4.23 (0.36) | 1.76 (5.71) | 0.22 (19.22) | 0.00 |
| 24 | 92.29 (0.21) | 0.35 (6.66) | 4.60 (1.95) | 2.76 (3.87) | 0.39 (23.47) | 0.00 |
| 60 | 90.29 (2.00) | 0.33 (9.09) | 4.48 (11.25) | 4.90 (34.30) | 2.14 (86.23) | 0.68 |

Example 5

Example 5 demonstrates the utilization of an antioxidant to retard oxidation of hPTH(1-34) agent. Table 15 lists the seven formulations that were prepared for the stability study.

TABLE 15

| Formulation | Formulation Composition (% w/w) |
|---|---|
| A | 25% PTH |
| B | 25% PTH, 0.5% methionine |
| C | 25% PTH, 1% methionine |
| D | 25% PTH, 3% methionine |
| E | 25% PTH, 0.5 mM EDTA |
| F | 25% PTH, 1 mM EDTA |
| G | 25% PTH, 3 mM EDTA |

Table 16 highlights the results of a 3 month stability study. Three peaks detected by RPHPLC at Relative Retention Times of 0.36, 0.53 and 0.68 were attributed to oxidized species of hPTH(1-34) and are denoted Oxid 1, 2 and 3, respectively. In all cases, the Oxid 3 species was the predominant oxidation product.

TABLE 16

| | Oxidation (%) | | | |
|---|---|---|---|---|
| | Oxid 1 RT = 0.36 | Oxid 2 RT = 0.56 | Oxid 3 RT = 0.68 | Total Oxid |
| Time Point 0 Months Formulation | | | | |
| Control | 0.00 | 0.14 | 0.31 | 0.45 |
| 0.5% Methionine | 0.00 | 0.13 | 0.28 | 0.41 |
| 1% Methionine | 0.00 | 0.12 | 0.29 | 0.41 |
| 3% Methionine | 0.00 | 0.12 | 0.27 | 0.39 |
| 0.5 mM EDTA | 0.00 | 0.12 | 0.26 | 0.38 |
| 1 mM EDTA | 0.00 | 0.14 | 0.28 | 0.42 |
| 3 mM EDTA | 0.00 | 0.15 | 0.30 | 0.45 |
| Time Point 1 Months Formulation | | | | |
| Control | 0.00 | 0.22 | 0.46 | 0.68 |
| 0.5% Methionine | 0.00 | 0.24 | 0.49 | 0.73 |
| 1% Methionine | 0.00 | 0.20 | 0.47 | 0.67 |
| 3% Methionine | 0.00 | 0.14 | 0.36 | 0.50 |
| 0.5 mM EDTA, | 0.00 | 0.13 | 0.27 | 0.40 |
| 1 mM EDTA | 0.00 | 0.14 | 0.29 | 0.43 |
| 3 mM EDTA | 0.00 | 0.18 | 0.36 | 0.54 |
| Time Point 3 Months Formulation | | | | |
| Control | 0.01 | 0.33 | 0.73 | 1.06 |
| 0.5% Methionine | 0.01 | 0.31 | 0.67 | 0.98 |
| 1% Methionine | 0.02 | 0.26 | 0.61 | 0.89 |
| 3% Methionine | 0.00 | 0.18 | 0.50 | 0.68 |
| 0.5 mM EDTA | 0.00 | 0.17 | 0.39 | 0.57 |
| 1 mM EDTA | 0.01 | 0.17 | 0.41 | 0.58 |
| 3 mM EDTA | 0.01 | 0.17 | 0.41 | 0.59 |

In summary, the formulation devoid of antioxidants yielded the highest percentage of total oxidized product and addition of methionine or EDTA retarded oxidation. The results indicate that methionine retards oxidation in a concentration dependant manner. However, EDTA did not exhibit this phenomenon. Addition of 0.5 mM EDTA to a formulation was as effective as 3 mM in retarding oxidation. Moreover, the results indicate that EDTA is more effectual in impeding oxidation than methionine.

Figure 13:
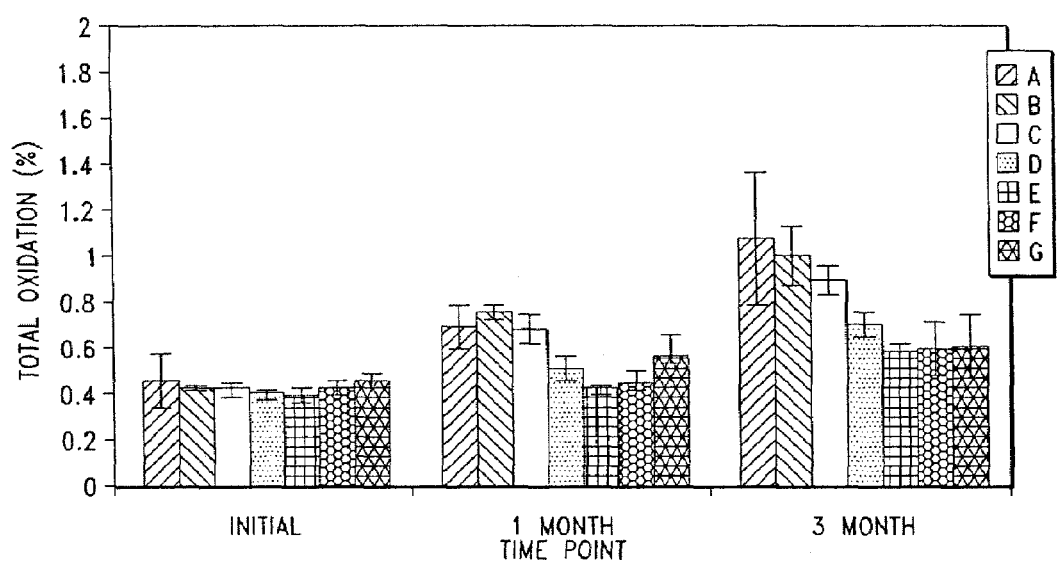
FIG. 13 is a graph illustrating the oxidation of a PTH-based agent with and without antioxidants over time, according to the invention.

These results are graphically illustrated in FIG. 13, which provides the sum of oxidized species of hPTH (1-34).

Example 6

In this example, transdermal delivery of a PTH-based agent using a coated microprojection member was compared to conventional, subcutaneous delivery of teriparatide PTH (Forteo™). A dose-finding study was conducted with 10 healthy, young females that received two treatments, separated by at least five days, according to randomly assigned sequence of 20 μg subcutaneous delivery of Forteo™ and 30 μg transdermal delivery of a PTH-based agent by coated microprojection. Bioavailability of transdermally delivered PTH was determined in 20 healthy, young females by administering two treatments, separated by at least five day, according to randomly assigned sequence of 40 μg subcutaneous delivery of Forteo™ and 30 μg transdermal delivery of a PTH-based agent by coated microprojection.

In the dose-finding study, two participants dropped out, eleven subjects participated and eight generated usable data. It was determined that three subjects had measurable PTH plasma levels following subcutaneous injection and eight subjects had measurable PTH plasma levels following transdermal delivery. In the bioavailability study, 20 subjects completed the study, with 15 subjects demonstrating measurable PTH plasma levels following subcutaneous delivery and 20 subjects demonstrating measurable PTH plasma levels following transdermal delivery.

Figure 14:
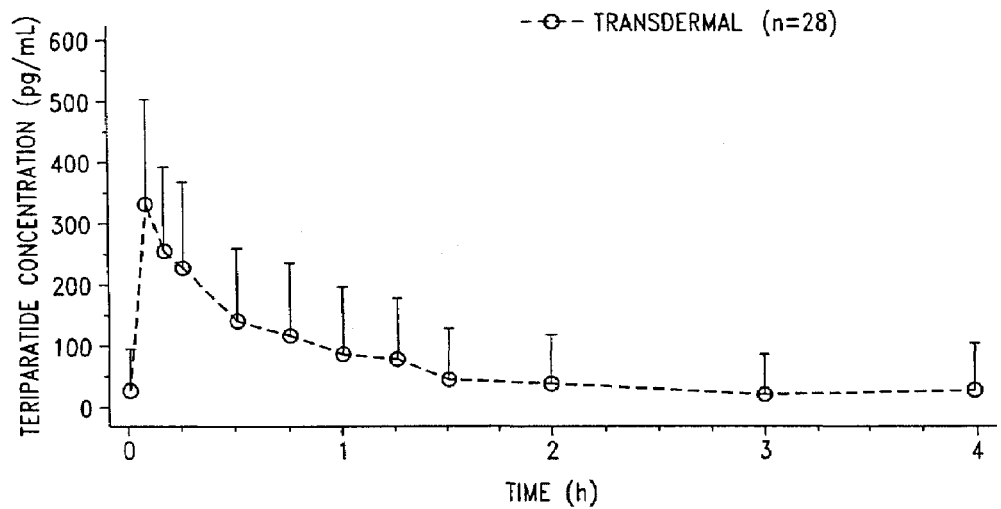
FIG. 14 is a graph illustrating the plasma concentration of a PTH-based agent following transdermal delivery, according to the invention.
Figure 15:
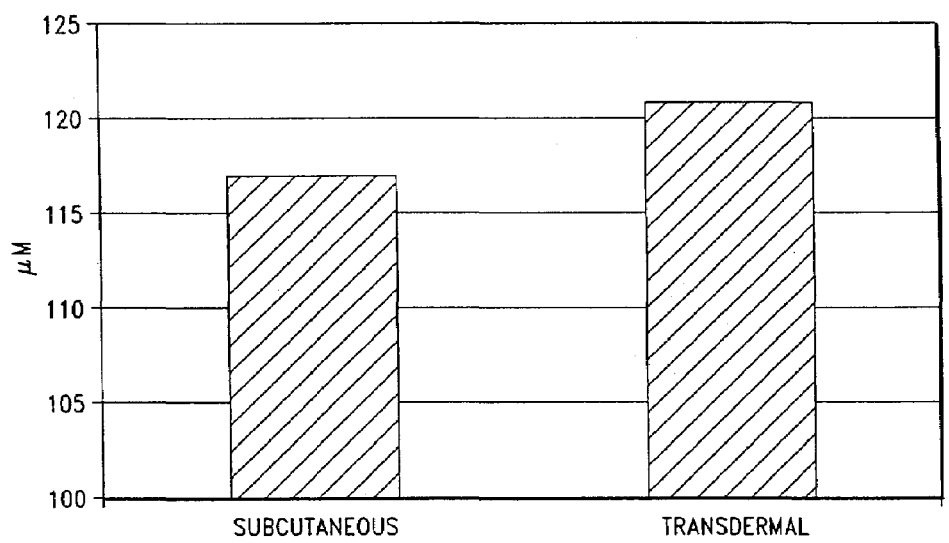
FIG. 15 is a graph illustrating urinary concentrations of cAMP that reflects the bioavailability of a PTH-based agent, according to the invention.

As shown in FIG. 14, transdermal delivery of a PTH-based agent yields effective absorption into the blood stream. FIG. 12 further reflects a preferred pulsatile concentration profile of the PTH agent, i.e., rapid on-set and rapid off-set after reaching Cmax. Further, as shown in FIG. 15, the biological activity of PTH following transdermal delivery is comparable to that following subcutaneous delivery as evidenced by increased levels of urinary cAMP excretion.

Figure 16:
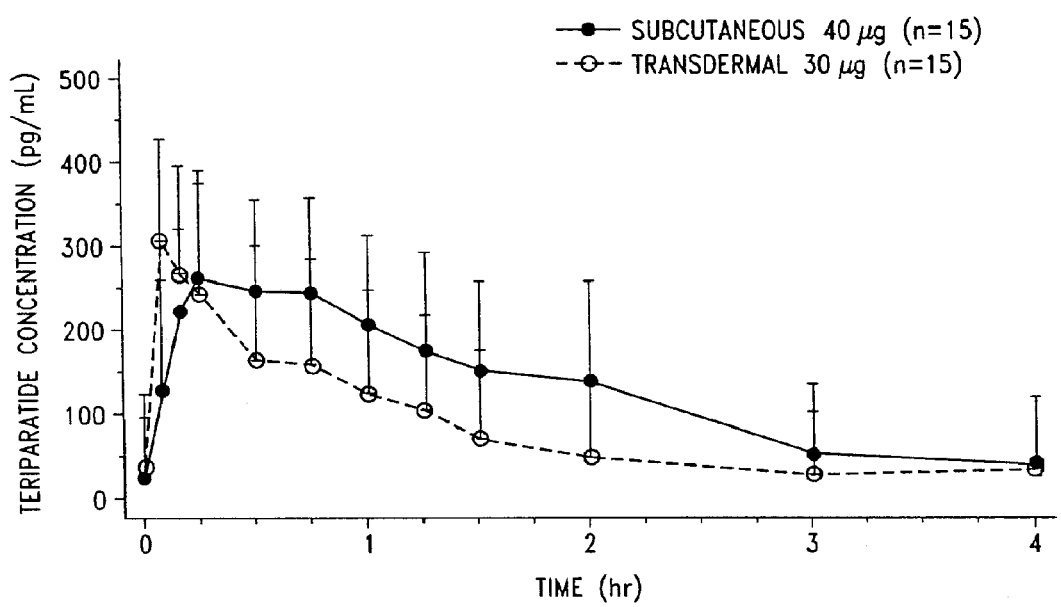
FIG. 16 is a further graph comparing plasma concentration of a PTH-based agent following transdermal and subcutaneous delivery, according to the invention.

The plasma concentration of PTH following subcutaneous delivery and transdermal delivery is compared in FIG. 16, which further demonstrates rapid absorption following transdermal delivery. FIG. 16 similarly reflects a preferred pulsatile concentration profile of the PTH-based agent, i.e., rapid on-set and rapid off-set after reaching Cmax.

The PK/PD results of the subcutaneous and transdermal delivery are further provided in Table 17, which indicate similar bioavailability of PTH.

TABLE 17

| Parameter | Forteo ™ Subcutaneous delivery 40 μg | Coated microprojection transdermal delivery 30 μg | P-Value |
|---|---|---|---|
| Tmax (hr) | 0.58 | 0.13 | <0.0001 |
| Cmax (ng/mL) | 0.22* | 0.32 | 0.04 |
| AUC (h · ng/mL) | 0.75 (cv = 152%) | 0.94 (cv = 216%) | 0.28 |
| ΔcAMP (μM) | 117 (n = 19) p < 0.0001 | 121 (n = 18) p = 0.0014 | 0.90 |

*normalized to 30 μg dose

Safety of transdermal delivery was also assessed during this experiment. Generally, transdermal delivery via coated microprojections compared favorably to the conventional subcutaneous delivery with similar proportions of subjects reporting adverse effects, but none were serious. Nausea and vomiting were more common with subcutaneous delivery.

As will be appreciated by one having ordinary skill in the art, the present invention provides numerous advantages. For example, a microprojection based apparatus and method has the advantage of transdermal delivery of a PTH-based agent exhibiting a PTH-based agent pharmacokinetic profile similar to that observed following subcutaneous administration. Another advantage is transdermal delivery of a PTH-based agent with rapid on-set of biological action. Yet another advantage is transdermal delivery of a PTH-based agent with sustained biological action for a period of up to 8 hours. Further, transdermal delivery from a microprojection array coated with a 10-100 μg dose of teriparatide (hPTH (1-34)) results in a plasma $C_{max}$ of at least 50 pg/mL after one application.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A device for transdermally delivering a PTH-based agent to a patient, comprising:
   a microprojection member having a plurality of microprojections that are adapted to pierce the stratum corneum of the patient; and
   a biocompatible coating disposed on said microprojection member, said coating comprising a hPTH acetate, hydrochloric acid, Tween, sucrose, and EDTA.

2. A device for transdermally delivering a PTH-based agent to a patient, comprising:
   a microprojection member having a plurality of microprojections that are adapted to pierce the stratum corneum of the patient; and
   a biocompatible coating disposed on said microprojection member, said coating being formed from a coating formulation comprising 20% hPTH(1-34) or salts thereof, 20% sucrose, 0.6% HCl, 0.2% Tween 20, and 0.03% EDTA and is at a dose of approximately 10-1000 µg that results in a plasma $C_{max}$ of at least 50 pg/ml after a single application.

* * * * *